US010968473B2

(12) United States Patent
Sutra et al.

(10) Patent No.: US 10,968,473 B2
(45) Date of Patent: Apr. 6, 2021

(54) METHOD, SYSTEM AND COMPUTER PROGRAM PRODUCT FOR DETERMINING THE PRESENCE OF MICROORGANISMS AND IDENTIFYING SAID MICROORGANISMS

(71) Applicants: BIOMERIEUX, Marcy-l'Etoile (FR); COMMISSARIAT A L'ENERGIE ATOMIQUE ET AUX ENERGIES ALTERNATIVES, Paris (FR)

(72) Inventors: Guillaume Sutra, Palaiseau (FR); Philippine Barlas, La Buisse (FR); Delphine Archeny, Chalamont (FR); Géraldine Durand, Les Avenières (FR); Corine Fulchiron, Serrieres de Briord (FR); Jean-Francois Gorse, Charnay (FR); Guillaume Perrin, Tassin la Demi-Lune (FR)

(73) Assignee: Biomerieux, Marcy-l'Etoile (FR)

( * ) Notice: Subject to any disclaimer, the term of this patent is extended or adjusted under 35 U.S.C. 154(b) by 82 days.

(21) Appl. No.: 16/325,541

(22) PCT Filed: Aug. 30, 2017

(86) PCT No.: PCT/EP2017/071775
§ 371 (c)(1),
(2) Date: Feb. 14, 2019

(87) PCT Pub. No.: WO2018/041900
PCT Pub. Date: Mar. 8, 2018

(65) Prior Publication Data
US 2019/0203257 A1 Jul. 4, 2019

(30) Foreign Application Priority Data

Sep. 2, 2016 (EP) ..................................... 16187153
Sep. 5, 2016 (EP) ..................................... 16306113

(51) Int. Cl.
*G06K 9/62* (2006.01)
*C12Q 1/04* (2006.01)
(Continued)

(52) U.S. Cl.
CPC ............... *C12Q 1/045* (2013.01); *C12Q 1/04* (2013.01); *G06K 9/0014* (2013.01);
(Continued)

(58) Field of Classification Search
CPC ...... C12Q 1/04–1/16; G06T 7/12; G06T 7/11; G06T 2207/20112–2207/20168;
(Continued)

(56) References Cited

U.S. PATENT DOCUMENTS

2004/0253660 A1* 12/2004 Gibbs ................... C12Q 1/045
435/34
2008/0153125 A1* 6/2008 Buttry ................... C12M 23/22
435/30
2015/0087017 A1 3/2015 Iizumi et al.

FOREIGN PATENT DOCUMENTS

EP 2520923 11/2012

OTHER PUBLICATIONS

Mukherjee et al., "Bacterial colony counting using distance transform", International Journal of Bio-Medical Computing 38 (1995) 131-140. (Year: 1995).*

(Continued)

*Primary Examiner* — Brian Werner
(74) *Attorney, Agent, or Firm* — McDonnell Boehnen Hulbert & Berghoff LLP

(57) ABSTRACT

A method and a system for determining the presence of at least one determined microorganism in a Petri dish comprising one or more colonies of microorganisms and a
(Continued)

culture medium, and a computer program product which, when executed, allows the method of the invention to be performed.

18 Claims, 17 Drawing Sheets

(51) Int. Cl.
    *G06T 7/11*     (2017.01)
    *G06T 7/162*     (2017.01)
    *G06T 7/00*     (2017.01)
    *G06T 7/136*     (2017.01)
    *G06K 9/00*     (2006.01)
    *G06T 5/30*     (2006.01)
    *G06T 5/50*     (2006.01)

(52) U.S. Cl.
    CPC .......... *G06K 9/00147* (2013.01); *G06T 5/30* (2013.01); *G06T 5/50* (2013.01); *G06T 7/0016* (2013.01); *G06T 7/11* (2017.01); *G06T 7/136* (2017.01); *G06T 7/162* (2017.01); *G06T 2207/10024* (2013.01); *G06T 2207/20036* (2013.01); *G06T 2207/20076* (2013.01); *G06T 2207/20224* (2013.01); *G06T 2207/30024* (2013.01)

(58) Field of Classification Search
CPC . G06T 7/187; G06T 5/30; G06T 2207/20224; G06T 2207/30024; G06K 9/0014; G06K 9/00127–9/00147
See application file for complete search history.

(56) References Cited

OTHER PUBLICATIONS

Weixing Wang, "Colony image acquisition system and segmentation algorithms", Optical Engineering 50(12), 123001 (Dec. 2011), cover sheet and pp. 123001-1 through 123001-9. (Year: 2011).*
Pedro F. Felzenszwalb, (2004), "Efficient Graph-Based Image Segmentation", International Journal of Computer Vision, vol. 59 (2), pp. 167-181.
Ferrari et al., "Multistage classification for bacterial colonies recognition on solid agar images", 2014 IEEE International Conference on Imaging Systems and Techniques (IST) Proceedings, IEEE, Oct. 14, 2014, pp. 101-106.
International Search Report and Written Opinion dated Oct. 9, 2017 for International Application No. PCT/EP2017/071775, 26 pages.

* cited by examiner

- 500 — obtaining a first original image
- 502 — determining the edge of the Petri dish
- 504 — separating each colour channel
- 506 — combining G and B colour channel images
- 508 — determining a threshold value
- 510 — applying the segmentation formula
- 512 — applying a morphological operation
- 514 — obtaining a second original image
- 516 — applying a dilatation operation
- 518 — dividing the HaloMask and the CultureMedium into pixel patches
- 520 — calculating median pixel values of the HaloMask and the CultureMediumMask
- 522 — determining the dilation size value
- 524 — applying the features formula
- 526 — classifying the features values of pixel patches
- 528 — comparing the features values of pixel patches with a threshold value
- 530 — determining the presence of haemolytic bacteria

FIG. 5

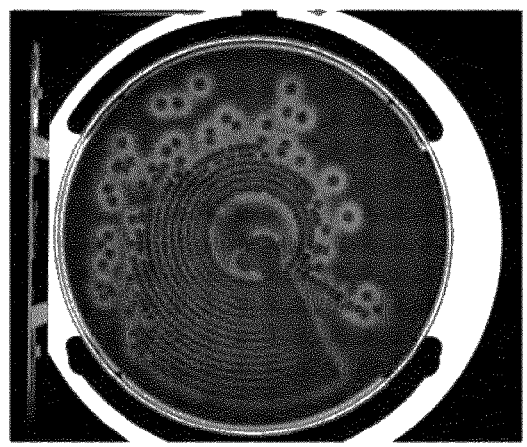
FIG. 6
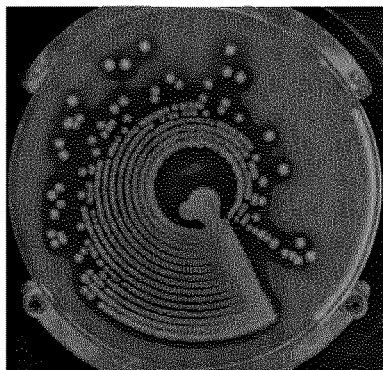 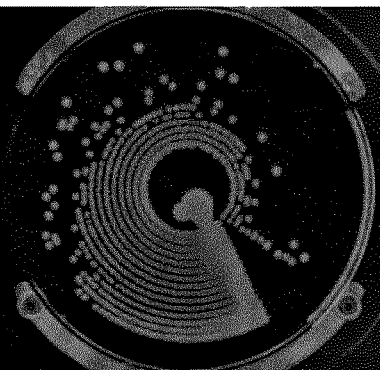 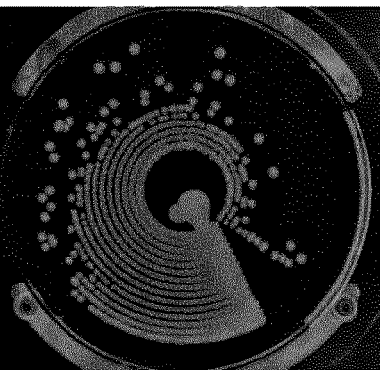
FIG. 7a  FIG. 7b  FIG. 7c
FIG. 8

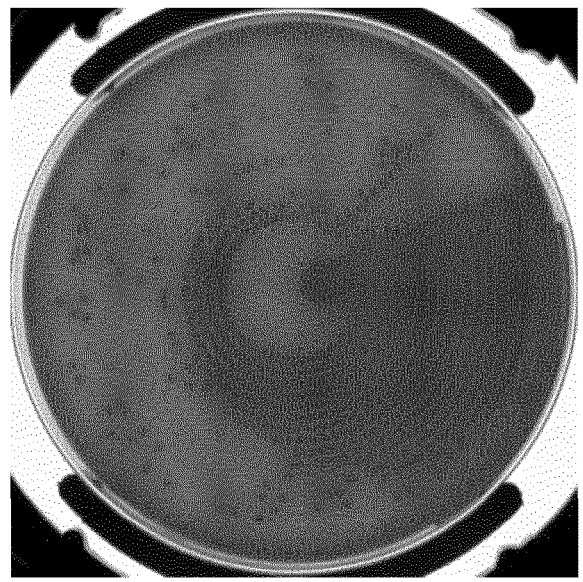
FIG. 20
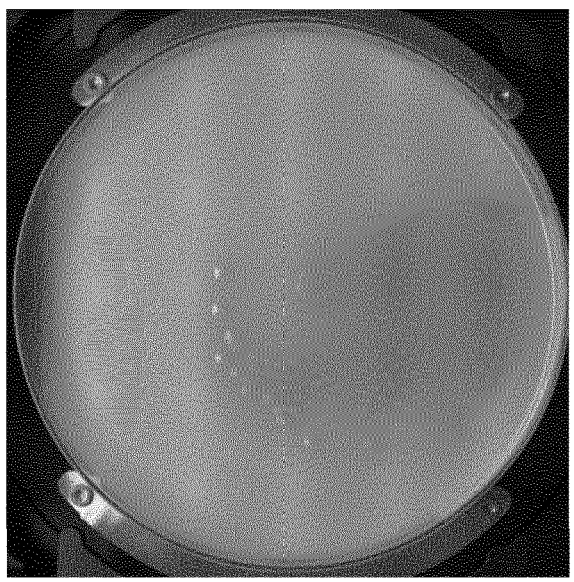 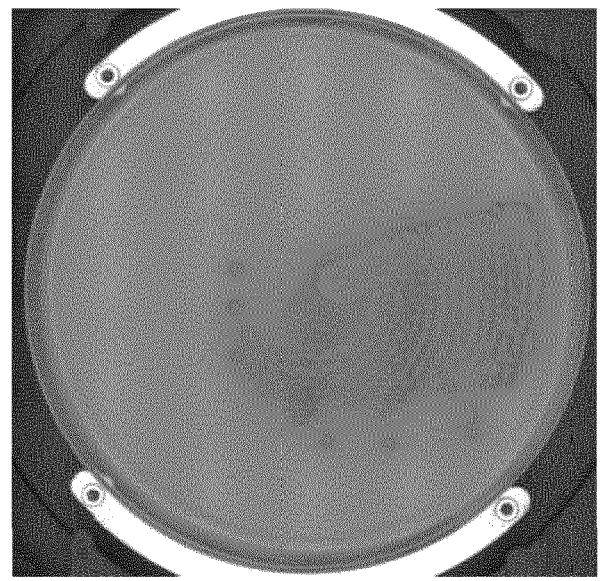
FIG. 21 FIG. 22

METHOD, SYSTEM AND COMPUTER PROGRAM PRODUCT FOR DETERMINING THE PRESENCE OF MICROORGANISMS AND IDENTIFYING SAID MICROORGANISMS

CROSS REFERENCE TO RELATED APPLICATIONS

This application is a U.S. national phase application under 35 U.S.C. § 371 of International Patent Application No. PCT/EP2017/071775, filed Aug. 30, 2017, which claims the benefit of priority of European Patent Application No. 16187153.8, filed Sep. 2, 2016 and European Application Patent Application No. 16306113.8, filed Sep. 5, 2016.

FIELD OF THE INVENTION

The present invention relates to the domain of microbiological analysis for analysing biological samples in a Petri dish, said biological samples comprising microorganisms, and more specifically to a method, system and computer program for determining the presence of microorganisms such as bacteria and identifying said microorganisms within the Petri dish.

BACKGROUND OF THE INVENTION

It is well-known in the domain of microbiology that analysis is carried out on the growth of biological samples comprising, for example, microorganisms, cellular or subcellular extracts, in order to determine the presence of specific bacteria and to identify said bacteria. Thus, a corresponding disease can be diagnosed.

In the prior art, some solutions exist to identify a bacteria. The solutions are based on methods comprising a supervised learning algorithm which uses criteria called descriptors. The descriptors relate to the colour, the form and the structure of the bacteria.

Such methods also operate with a step for determining the location of isolated colonies of bacteria. The location may be provided either by the user in a semi-automated manner or by applying a specific segmentation algorithm in an automated manner. However, both of these methods of providing the location are inaccurate and generate some errors which lead to an incorrect determination of the location.

The published patent application US 2015/0087017 discloses a method for an automated classification of bacterial colonies. The method is based on a classification step of bacterial colonies within a Petri dish, said classification step being based on criteria such as colour, shape and outline for each bacterial colony.

However, such an automated method does not apply for the analysis of the content of a Petri dish. Indeed, the environment around the bacterial colonies in the Petri dish also has to be analysed to identify a specific biological phenomenon related to said bacterial colonies and their interaction with the culture medium. Such biochemical reactions are used by biologists to distinguish between different microorganisms and allow for making or ruling out diagnostic hypothesis.

For instance, in respect of analysing the growth of microorganisms in a Petri dish containing blood agar culture medium, the methods of the prior art include a step for identifying the nature of the haemolysis phenomenon to determine the level to which the blood cells in the agar medium are degraded in order to characterize specific microorganisms. The haemolysis phenomenon relates to the capability of certain microorganisms to produce a protein which is able to destroy the blood cells of the agar. There are three types of haemolysis phenomenon, designated by alpha, beta and gamma as follows:

the alpha-haemolysis phenomenon produces a greenish discoloration that surrounds a bacterial colony growing on the blood agar. This type of haemolysis phenomenon represents a partial decomposition of the hemoglobin of the red blood cells of the blood agar;

the Beta haemolysis phenomenon represents a total decomposition of the hemoglobin of the red blood cells in the vicinity of a bacterial colony.

the Gamma haemolysis phenomenon corresponds to the absence of any decomposition in the area around a bacterial colony.

In other situations the interaction between the bacteria and the medium generates visible artefacts surrounding the colonies such as the appearance of a specific colour. These colour changes are due to chemical reactions between the culture medium and metabolites produced by the bacteria, wherein said chemical reactions can be interpreted as positive or negative reactions depending on the nature of the microorganism itself. Nowadays, such a step is provided by the user who has to watch the content of the Petri dish to determine the nature of the haemolysis phenomenon or colour changes around the colonies. However, such a human analysis may lead to errors. In addition, in the situation where there is an increased number of Petri dishes to be analysed, said identification step is a time consuming process.

Thus, there is a need to improve the methods of the prior art to allow an automated identification of a biological element in a Petri dish in an efficient manner.

SUMMARY OF THE INVENTION

According to one aspect of the present invention, there is provided a method for determining the presence of at least one determined microorganism (such as at least one determined bacterium) in a Petri dish comprising one or more colonies of microorganisms and a culture medium, said culture medium being adapted to allow the one or more colonies of microorganisms and said at least one determined microorganism, if present, to grow under suitable growth conditions, the method comprising:

obtaining at least an initial image of the Petri dish, wherein the first initial image comprises one or more visible pixels, each pixel being associated with a pixel value;

obtaining a first processed image of the Petri dish by applying a first process to the at least one initial image, wherein visible pixels of the first processed image only relate to the pixels associated with the one or more colonies of microorganisms;

obtaining a plurality of second processed images of the Petri dish by applying a second process to the first processed image, wherein visible pixels of the second processed image only relate to the pixels associated with the one or more colonies of microorganisms and a surrounding zone around said one or more colonies of microorganisms;

obtaining a plurality of third processed images of the Petri dish by calculating the difference between the at least one initial image and the plurality of second processed images, wherein the plurality of third processed images comprises visible pixels which only relates to pixels associated with the culture medium;

obtaining a plurality of fourth processed images of the Petri dish by calculating the difference between the plurality of second processed images and the first processed image, wherein visible pixels of the plurality of fourth processed images only relate to pixels associated with the surrounding zone;

determining features values associated with the plurality of the third and the fourth processed images by calculating the difference values between the average pixel values of the plurality of the third processed image and the average pixel values of the plurality of the fourth processed image for at least each colour channel of the Red Green Blue (RGB) colour channels;

determining a value of an indicator of the presence of the at least one determined microorganism within the surrounding zone in the Petri dish by classifying the determined features values;

comparing the value of the indicator with a threshold value;

depending on the result of the comparison, determining the presence of the at least one determined microorganism within the surrounding zone in the Petri dish.

In the context of the present application, the term "average pixel values" refers to:

the arithmetic mean of pixel values, or the median value of pixel values.

According to a preferred embodiment of the invention, the features values associated with the plurality of the third and the fourth processed images are determined by calculating the difference values between the median pixel values of the plurality of the third processed image and the median pixel values of the plurality of the fourth processed image for at least each colour channel of the Red Green Blue (RGB) colour channels.

Preferably, the first process is a segmentation process.

The method according to the present invention provides an automated analysis of the content of a Petri dish based on an automated identification of a specific zone around colonies of microorganisms and an automated determination of the presence of bacteria such as beta-haemolytic or Proteus bacteria which are respectively associated with a biological phenomenon such as the haemolysis phenomenon or Proteus infection. Thus, the present method avoids the operation of a visual identification step and/or a visual determination step.

The method according to the present invention comprises a step for identifying a specific zone around colonies of microorganisms in the Petri dish, wherein said specific zone may comprise bacterial colonies or bacterial clusters of colonies.

According to a further aspect of the invention, there is provided a system for determining the presence of at least one determined microorganism (such as at least one determined bacterium) in a Petri dish comprising one or more colonies of microorganisms and a culture medium, said culture medium being adapted to allow the one or more colonies of microorganisms and said at least one determined microorganism, if present, to grow under suitable growth conditions, wherein the system comprises an imaging system for obtaining at least one initial image of the Petri dish, and a processing system, said processing system comprising:

a first processing unit for obtaining a first processed image of the at least one initial image of the Petri dish, wherein visible pixels of the first processed image only relate to the pixels associated with the one or more colonies of microorganisms;

a second processing unit for obtaining a plurality of second processed images of the first processed image of the Petri dish, wherein visible pixels of the second processed images only relate to the pixels associated with the one or more colonies of microorganisms and a surrounding zone around said one or more colonies of microorganisms;

a calculation unit for obtaining a plurality of third processed images of the Petri dish by calculating the difference between a second initial image and the second processed images, wherein visible pixels of the third processed images only relates to pixels associated with the culture medium, and for obtaining a plurality of fourth processed images of the Petri dish by calculating the difference between the second processed images and the first processed image, wherein visible pixels of the fourth processed images only relate to pixels associated with the surrounding zone;

a features extraction unit for determining features values associated with the plurality of the third and the fourth processed images by calculating the difference values between the average pixel values of the third processed images and the average pixel values of the fourth processed images for at least each colour channel of RGB colour channels;

and an analysis unit for determining a value of an indicator of the presence of the at least one determined microorganism within the surrounding zone in the Petri dish, comparing the value of the indicator with a threshold value; and determining the presence of the at least one determined microorganisms within the surrounding zone in the Petri dish, depending on the result of the comparison.

As previously indicated, according to a preferred embodiment of the invention, the features values associated with the plurality of the third and the fourth processed images are determined by calculating the difference values between the median pixel values of the plurality of the third processed image and the median pixel values of the plurality of the fourth processed image for at least each colour channel of the Red Green Blue (RGB) colour channels.

According to a further aspect of the invention, there is provided a computer program product comprising instructions which, when executed, cause a programmable data processing apparatus to perform steps of the method according to the invention.

BRIEF DESCRIPTION OF THE DRAWINGS

Reference will now be made, by way of example, to the accompanying drawings, in which:

FIG. 5 shows a flowchart of the method for determining the presence of haemolytic bacteria, according to an embodiment of the present invention;

FIG. 6 represents the original image of the Petri dish containing blood agar and haemolytic bacteria, said original image relating to a backlight illumination, according to an embodiment of the present invention;

FIGS. 7*a*, 7*b* and 7*c* respectively show the red, green and blue colour channel image of the original image with a median bottom view, according to an embodiment of the present intention;

FIG. 8 shows a binary image called GrowthMask of the original image according to an embodiment of the present invention;

FIG. 20 shows an original image of a Petri dish containing an opaque culture medium such as an opaque CPS with Proteus bacteria, according to an embodiment of the present invention;

FIGS. 21 and 22 respectively show an image of the Petri dish of FIG. 20 related to the left bottom annular view and the top annular view, according to an embodiment of the present invention;

DETAILED DESCRIPTION OF THE PREFERRED EMBODIMENTS

The description below discloses the invention in a sufficiently clear and complete manner, based on specific examples. However, the description should not be understood as limiting the scope of protection to the specific embodiments and examples described below.

In the description below, the term "Petri dish" defines an assembly of a Petri plate and a lid to cover the Petri plate. The Petri dish may comprise a serigraphy shown on the Petri plate or on the lid.

In the description below, the term "pixel" relates to a position in an image and the term "pixel value" refers to the detected value of the corresponding captured intensity of the pixel in said image.

In the description below, the term "dark pixel" relates to a pixel having a pixel value of 0.

In the description below, the term "visible pixel" relates to a pixel having a value other than 0, also known as a bright pixel.

The described calculation operations relate to operations associated with pixel values of the related images.

In the description below, the representation of the surface of the Petri dish takes place in an orthonormal space x, y, z where z is a function of x and y, such as $z=f(x,y)$.

In the description below, the pixels associated with the Petri dish define a zone in an image called a DishMask.

In the description below, the pixels associated with the culture medium define a culture medium zone in an image called a CultureMedium Mask.

In a similar manner, the pixels located around the colonies of microorganisms define a surrounding zone or a halo zone in an image called a HaloMask.

In the description below the term "original image" relates to an image of the Petri dish being acquired with an image capture device.

In the description below, the term "initial image" relates to an image of the Petri dish, wherein the initial image may relate to an original image or an image having been processed within an imaging system after being acquired with the image capture device.

Figure 1:
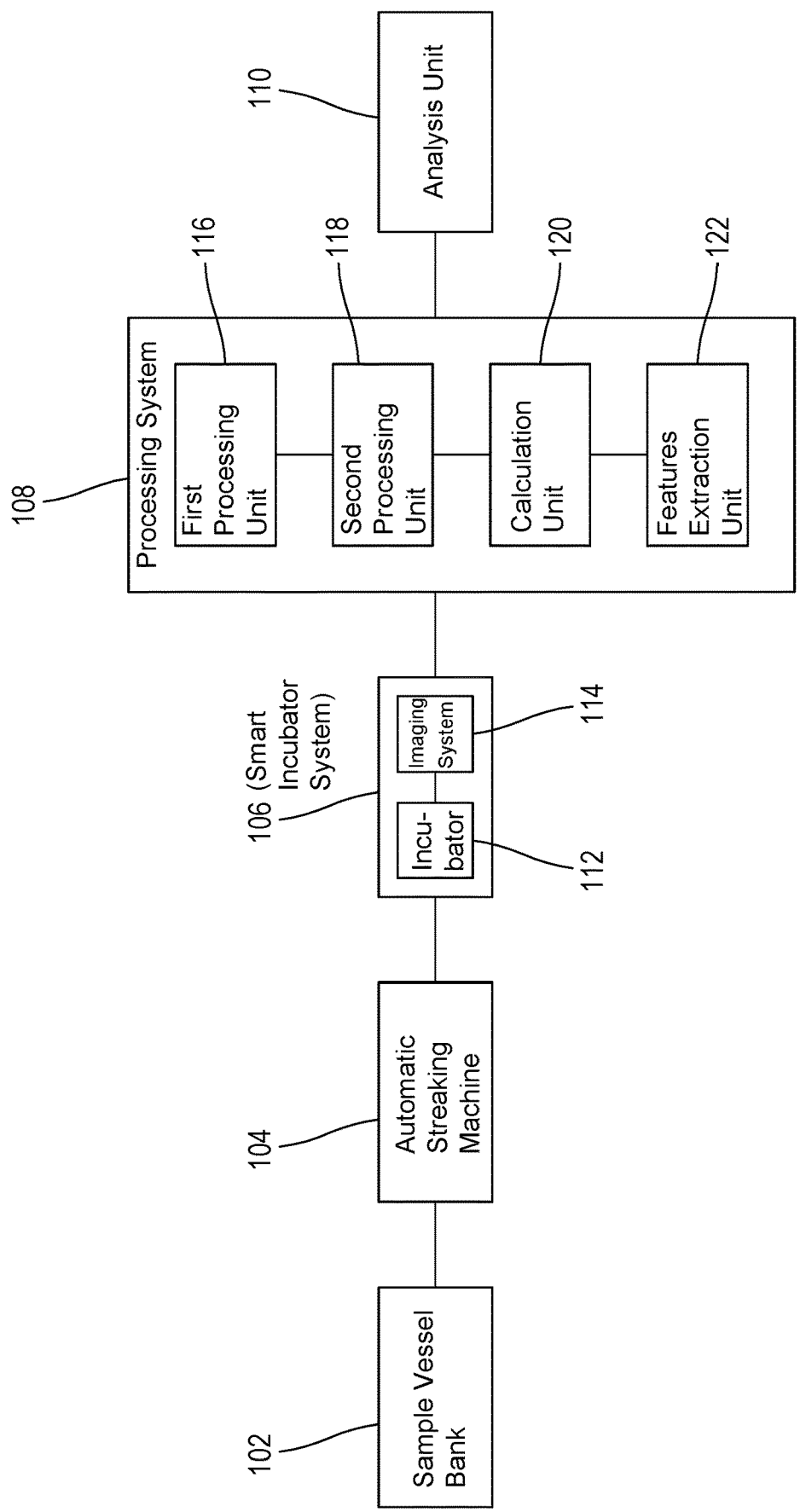
FIG. 1 represents a simplified diagram of the system according to an embodiment of the present invention.

FIG. 1 shows an example of a system 100 according to the present invention. The system 100 includes a sample vessel bank 102, an automatic streaking machine 104, a smart incubator system 106, a processing system 108 and an analysis unit 110.

The sample vessel bank 102 manually or automatically produces sample vessels into which biological samples can be grown and analysed. The sample vessel is typically a Petri dish, although other vessels may also be used. Accordingly, reference to a Petri dish herein is not intended to be limitative.

The sample vessel bank 102 adds an appropriate culture medium to the Petri dish to enable the biological sample to grow.

The automatic streaking machine 104 applies a biological sample to the Petri dish and then distributes the biological sample in a known manner. For example, in a Petri dish, the biological sample is applied using a comb having a length approximately equal to the radius of the Petri dish. The comb is applied and then turned to spread the biological sample over the surface of the Petri dish. An example of a suitable automatic streaking machine 104 is commercialized by the applicant under the PREVI® Isola brand name.

Once the biological sample has been distributed over the culture medium in the Petri dish, the Petri dish is passed to the next stage of the process, i.e. the smart incubator system 106, manually by an operator or by means of a conveyor belt or other automated system.

The smart incubator system 106 includes an incubator 112 and an imaging system 114. The Petri dish is introduced into the smart incubator system 106 and is incubated for a predetermined time at a predetermined temperature. This causes the biological sample to grow producing a number of colonies of microorganisms over the surface of the culture medium within the Petri dish. Once the Petri dish has been incubated as required, the Petri dish is passed to the imaging system 114. The imaging system 114 is a system for generating images of the colonies and cultures generated in the system 100 as a whole. The details of the imaging system 114 will be described further below.

The images are used in the first stage of analysis of the biological samples. This stage can identify colonies and other aspects of the biological sample to aid and facilitate further activities and functions of the overall system 100.

After the images of the Petri dish have been produced, the Petri dish is then passed to the next stage of the process i.e. the processing system 108. This may be carried out automatically by a conveyor belt or other automated system, or by an operator.

The processing system 108 can take on a variety of different forms depending on the required biological sample analysis. For example, particular colonies may be extracted, based on the images, for further analysis or processing. Many other processes can be applied to the Petri dish at this time. If necessary, the Petri dish can be returned to the smart incubator system 106 for further growth and/or returned to the imaging system 114.

After all the necessary processing and imaging has been completed, the Petri dish may be passed to the analysis unit 110 by means of a manual or automated process.

Figure 2:
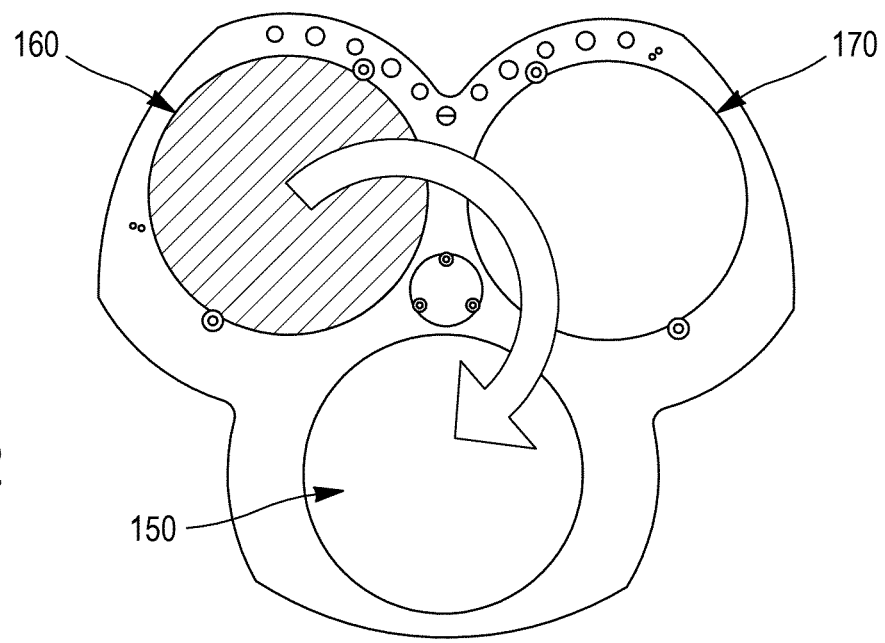
FIG. 2 represents a controller in the form of a wheel comprising a circular hole, a white background circle and a black background circle, according to an embodiment of the present invention.

As previously mentioned the smart incubator system 106 includes the imaging system. The imaging system 114 includes a base unit. The base unit includes the optics and control circuitry for generating red, green and blue backlighting illumination. The base unit may include a controller which may be in the form of a wheel that has three positions as shown in FIG. 2. These positions correspond to different illuminations which are "noBackground", "whiteBackground" and "blackBackground". The "noBackground" position relates to a circular hole 150 in the wheel. The "whiteBackground" position relates to a white background circle 160 in the wheel. The "blackBackground" position relates to a black background circle 170 in the wheel. No background is used for backlight, whilst white and black are used for all other types of illumination, depending on the nature of the sample.

Above the base unit, there is a sample holding unit. The sample holding unit may include a drawer which can slide in and out and includes a sample recess which is adapted to support a Petri dish. In addition, the sample holding unit includes four red, green and blue horizontal illumination sources. The four illumination sources are located rectilinearly around the sample recess and are independently controllable. In use, the top of the Petri dish is substantially in line with the top of the four horizontal illumination sources. The horizontal illumination sources allow the Petri dish to be illuminated with a horizontal or near horizontal beam.

It should be noted that the bottom of the sample recess is optically transmissive to allow the backlight illumination to illuminate the biological sample in use. The sample holding unit further includes the optics and controls required to operate the four horizontal illumination sources.

The sample holding unit may comprise an alternative orientation in which the biological samples are passed into position for imaging by a conveyor belt. The drawer may be replaced by a conveyor belt system having sample holding zones, each of which is transparent to allow backlighting to be used. The conveyor belt system can move the biological sample into an appropriate position and then the necessary images can be taken. The conveyor belt then moves the next biological sample into position for imaging and the first biological sample on to the next stage of processing. This enables images to be taken at different positions and when the biological sample is moving.

In a further alternative, the imaging system may include a robotic arm which is able to load Petri dishes into the sample holder or on to the conveyor belt. In addition, the robotic arm may remove the lid of the Petri dish prior to imaging and replace the lid thereafter. This can be done by inverting the Petri dish and causing the lid to fall off. Removing the lid ensures the lid does not produce reflections when the biological sample is illuminated by certain illumination sources.

In addition to movement into and out of the imaging zone, the sample holding unit may also include a mechanism to change the position of the biological sample relative to the normal position. For example, the sample holding unit may be able to orientate the sample to be at a specific angle to a specific beam. Other movements, for example rotation, of the biological sample can also be carried out with appropriate mechanisms. As a result, any relative movement of the biological sample and the illumination sources can be realized by moving either the biological sample in the sample holding unit or the illumination source. The variations are endless.

The imaging system 114 further includes a first intermediate unit which is situated above the sample holding unit. The first intermediate unit includes four rectilinearly positioned red, green and blue illumination sources. The illumination sources are adapted in use, to produce annular illumination onto the sample recess in the sample holding unit and are each independently controllable. The annular illumination can be adjusted to be incident on the sample from any appropriate direction, including lateral, non-lateral or any other appropriate orientation.

The imaging system 114 also includes a second intermediate unit. The second intermediate unit includes four rectilinearly positioned red, green and blue illumination sources. The illumination sources are directed upwards and reflect from the unit above to give rise to an inverse annular illumination which, in use, illuminates the sample in the sample recess. Each illumination source is independently controllable.

A head unit of the imaging system 114 is located above the second intermediate unit. The head unit includes white light illumination sources which are each independently controllable. The eight illumination sources are arranged, in use, to produce vertical illumination onto the sample recess.

The head unit also includes an image capture device 254, such as a camera which is directed towards the sample recess. Illumination from any combination of illumination sources from any of the units can be directed to the sample recess. The image capture device can then capture images from any biological samples in the sample recess which have been illuminated. The use and further processing of the images will be explained in greater detail below.

The head unit may also include a control pad which is used to operate the various light sources. In addition to the control circuitry and optics in each unit, which control the function thereof, there may be an overall control system. The overall control system may include a computer, a display unit, processing modules and image enhancing algorithms, image processing, and any other processes or techniques.

The overall control system may be used to control which illumination sources are used for specific applications. In addition, the overall control system may apply different image enhancing techniques and image processing for different applications. Image enhancing techniques are methods and techniques to enhance the quality of the image or to make pertinent information visible for an expert to view. Examples, described in greater detail below, include: fusion of different images such as vertical fusion or fusion for haemolysis, edge lighting correction, exposure time correction etc. Image processing is the extraction of information from images in order to provide decision support or automatic decisions. This does not necessarily include a modification of the image but instead a determination of higher level information/interpretation in an automated manner. Examples, described in greater detail below, include: detection of the dish ring, detection of marks, detection of growth (masses, isolated colonies, swarming), global decision on growth/no growth, etc.

The overall control system may be used to carry out any other function and/or control operation for the imaging system. These include, but are not limited to,
- loading and unloading the sample into the sample recess;
- checking and adjusting the positioning of the sample in the sample recess;
- controlling the level of luminance;
- controlling the balance of the red, green and blue components;
- controlling exposure time;
- controlling illumination combinations;
- testing the system;
- calibrating the system; and
- any other appropriate control based on the use and purpose of the analysis.

Each of the units forming the imaging system is capable of being moved relative to the other units. When this occurs, certain optical adjustments may be necessary to ensure the biological sample is illuminated by all sources.

The operation of the imaging system 114 will now be described in more detail with reference to FIG. 3.

Figure 3:
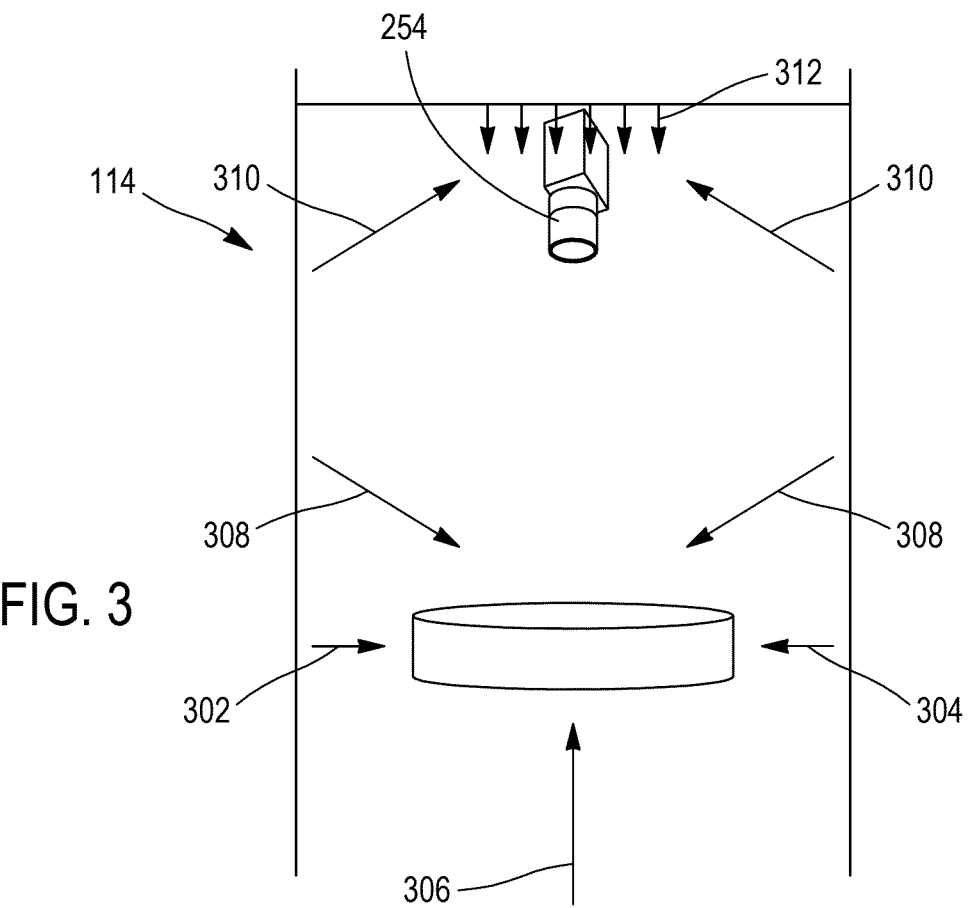
FIG. 3 is a simplified diagram of the imaging system, showing the different types of illumination beams applied to a Petri dish, according to an embodiment of the present invention.

FIG. 3 shows a schematic diagram of the imaging system 114 to demonstrate the various illumination sources and how they impact on a biological sample located in the imaging system 114. The sample may be illuminated by a near horizontal beam 302, 304 located in the same plane as the plane of the Petri dish which contains the biological sample. The near horizontal beam in fact includes components into and out of the paper in addition to those illustrated by references 302 and 304. The near horizontal beam 302, 304 is produced by the horizontal illumination sources in the sample holding unit.

The sample may also be illuminated by a backlight beam 306 generated by the base unit and underneath the Petri dish to emit in a vertical direction from the bottom of the imaging system 114 towards the top of the imaging system 114.

An annular beam or bottom annular beam 308 may also illuminate the biological sample 300 and is produced by the first intermediate unit located above the Petri dish. The bottom annular beam 308 is emitted with a determined angle towards the Petri dish. An inverse annular beam or top annular beam 310 produced by the second intermediate unit located above the Petri dish can also illuminate the Petri dish. The inverse annular beam 310 is emitted with a determined angle towards the top of the imaging system 114, away from the Petri dish and then reflected towards the Petri dish.

A vertical beam 312 can also illuminate the Petri dish and is generated by the illumination sources in the head unit.

The vertical beam and the backlight illumination apply illumination in a substantially perpendicular direction relative to the biological sample in the Petri dish. The optical axis of each of these illumination sources is accordingly also perpendicular to the biological sample. The near horizontal, the annular and inverse annular illuminations are not perpendicular to the Petri dish. Similarly therefore, the optical axes of these sources are non-perpendicular to the biological sample. The non-perpendicular sources provide a diverse range or alternative images to those achieved with perpendicular sources. These non-perpendicular sources provide additional and different optical features in any image created with them. This ensures that isolation and detection of colonies is improved.

The illumination sources shown in FIG. 3 and produced by the appropriate unit may be of any preferred type, such as light emitting diodes (LED) operating at red, green and blue (RGB) frequencies; a simple white light source; an ultra-violet (UV) source or any other appropriate radiation source. The illumination sources may comprise, for example, 322 LEDs including 64 white LEDs, 86 red LEDs, 86 green LEDs and 86 blue LEDs. The number of light sources in any location can vary from that shown and described herein. RGB illumination is provided at each location by a trio of three LEDs operating at each respective frequency. For different illumination sources there may be different combinations of RGB LEDs. Each type of illumination is provided by means of specific cards comprising specific arrangements of LEDs. The base unit produces the backlight beam 306 by means of two cards, each including a plurality of diodes arranged in threes. Each trio of LEDs 404 includes a red, green and blue LED. In total, 45 trios of LED are located on each card and are used to generate the backlight beam 306. Among each trio, the red, green and blue LEDs can be illuminated one at a time to produce one coloured illumination after the other.

In all instances of the illumination mentioned above the image of the biological sample is captured from above by the image capture device 254. It should be noted that the image capture device 254 may take a sequential set of images over a predetermined time period to measure the growth of colonies and other time related effects. In addition, the image capture device 254 may be a video camera for certain applications where growth progress of colonies, and the like, is being measured. Movement of the Petri dish may also be brought about by movement of the Petri dish into and out of the imaging system 114 by means of a suitable conveyor belt or robotic arm.

The image capture device 254 is adapted to take different types of images from different illumination sources. Typically a sequence of images is taken for a specific application. The sequence comprises the steps of illuminating the sample with a specific illumination or combinations of illumination, followed by taking a specific type of image, such as monochrome, black and white, or RGB with the relevant illumination. Then a next image is taken with a different type of illumination or combination thereof and the sequence continues until all the required images have been taken. The image capture device 254 is controlled within the sequence to take the appropriate type of image.

As previously mentioned, a biological sample in the imaging system 114 can be illuminated from a plurality of different light sources, which strike the sample from different directions. After the biological sample has been illuminated an image of the biological sample is taken from above. Each illumination highlights different aspects of the biological sample.

The backlight illumination shows detail of the Petri dish including any markings on the base thereof, the form of the edge and the lid of the Petri dish; and a detailed view of the layout and density of the colonies in the biological sample. This illumination provides information which can isolate colonies, determine the difference between similar colonies (for example a and R haemolytic species) and generally gives a view of the contents of the sample.

The near horizontal illumination is refracted and reflected by the sample and the contents thereof to form an image which can be used to isolate and eliminate artefacts. In addition, this image can be used to make corrections based on the absorption of illumination by the culture medium as will be described in further detail below. The image may also be used later to determine the percentage cover of the Petri dish by colonies to provide an estimate of colony concentration and to determine growth or no growth on non opaque culture media.

The annular illumination is directed towards the sample and is reflected or refracted to the image capture device 254 by the culture medium and any colonies which have been formed. The purpose of the image produced by this illumination is the ability to distinguish the colours of the culture medium and the colonies. The ability to identify colour is often an important tool for identifying specific microorganisms as some have very distinctive colouring. The overall result is a view which is the closest to that which a biologist would expect to see for a specific type of microorganism, for example, colours, colony aspects, etc. This is particularly important to identify the subtle changes in colouring in the culture medium and around the colonies. In addition, images produced by annular illumination allow detection of subtle variations of colours below and around the bacterial colonies in chromogenic media.

The lateral annular illumination is an illumination of only one of the four rectilinearly positioned sources. This gives an image having shadows which can be used to identify contours and relief. Each of the sources will give rise to different shadow effects as a result of the direction of illumination.

The inverse annular illumination is reflected from the head unit onto the sample. The sample then reflects or refracts the illumination to the image capture device 254. The image thus captured gives details of the contrast of the different colonies in the sample. This image can also contribute colour information. In addition, this image can provide texture information; aspect and colour of the colonies; information on swarming limits and certain information about the relief of the colonies, such as elevation, form and shape.

The inverse annular illumination produces a quasi-vertical illumination which enables visualization of changes in gradient. This gives texture and granularity information and is useful in detecting colonies which do not have much elevation but have surface irregularities. In one embodiment, a number of different images are taken using the inverse annular illumination and subsequently combined in order to deal with the possibility of saturation of the image.

The vertical illumination source illuminates the biological sample from above. The illumination is reflected by the biological sample and colonies to give an image which provides detailed contour information. This can be used to identify the relief of the biological sample and the height of colonies. This information can then be used to identify specific types of microorganisms as the relief of a colony is often very specific. For example, certain colonies are dome shaped, others are bumpy, other are flat, etc.

As described above, each of the illumination sources and directions can be used to accentuate and enhance different image characteristics. The examples described may be changed or adapted by using illumination from different sources and directions without departing from the scope of the present invention.

Furthermore, different wavelengths of illumination can be used for different applications, for example infra red and ultraviolet.

The imaging system 114 may create images from a combination of illumination sources to generate a composite image which can accentuate and enhance more than one characteristic of the image of the biological sample.

Another factor which can have an effect on the image generated is the type of culture medium used to grow the sample. Many different culture media exist; these include CPS which is a culture medium particularly adapted to identify E. coli, Proteus, and KESC using a urine sample; and COS which is a culture medium including blood which is useful in identifying haemolytic ability.

Different culture media, such as CPS and COS are quite different in nature and colour. As a result, illumination acting thereon may produce different types of image. As such, different illumination sources and combinations of sources may be used for different culture media.

As previously mentioned, the system 100 comprises a processing system 108 and an analysis unit 110. The processing system 108 comprises a first processing unit 116, a second processing unit 118, a calculation unit 120 and a features extraction unit 122.

The first processing unit 116 is capable of operating a first process, which is a segmentation process applied to an original image of the Petri dish such as backlight or bottom annular view and provided by the imaging system 114, for obtaining a binary image showing a visible separation line between the content of the Petri dish associated with the colonies of microorganisms and the content of the Petri dish associated with the culture medium. Thus, the first processing unit 116 provides a first processed image which is a binary image named a GrowthMask comprising visible pixels which only relate to pixels associated with the colonies of microorganisms.

The first processing unit 116 may also operate additional processes comprising a well-known edge detection process to locate the content of the Petri dish with respect to the edge of the Petri dish and a well-known combination process to combine two original images in a well-known process for removing image noise.

The second processing unit 118 is capable of operating a second process which is a dilation process being applied to the GrowthMask for obtaining a second processed image named Dilated(GrowthMask). The Dilated(GrowthMask) comprises visible pixels which only relate to pixels associated with the colonies of microorganisms and also to pixels associated with a surrounding zone around the colonies of microorganisms. The dilation parameter is defined so that the Dilated(GrowthMask) encompasses the surrounding zone. The dilation parameter is determined by the user as described below. The surrounding zone may relate to a zone showing another colour when compared to the colour of the microorganisms in the same image. The surrounding zone may also relate to a zone showing discolouring of the colour of the microorganisms or to a zone showing a new pigmentation when compared to the colour of the microorganisms in the same image.

The calculation unit 120 is capable of operating a third process relating to a difference calculation between two images for obtaining a resulting image. Thus, the calculation unit 120 is capable of calculating the difference between the original image of the Petri dish, i.e. the DishMask, and the GrowthMask to provide a third processed image named CultureMediumMask. The CultureMediumMask comprises visible pixels which only relate to pixels associated with the culture medium.

The calculation unit 120 is also capable of operating a fourth process relating to a difference calculation between the Dilated(GrowthMask) and the GrowthMask to provide a fourth processed image named HaloMask. The HaloMask comprises visible pixels which only relate to the surrounding zone.

The features extraction unit 122 is capable of operating a features extracting process for determining features values of the HaloMask and the CultureMediumMask. The features values relate to the pixel values of the HaloMask and the CultureMediumMask. The features extraction unit 122 calculates the difference between the average pixel values of the third processed image and the average pixel values of the fourth processed image for at least the three Red Green Blue (RGB) colour channels. As stated above, the term "average pixel values" refers to the arithmetic mean of pixel values or to the median value of pixel values.

The analysis unit 110 is capable of operating an analysis process based on the determined features values to determine the presence of bacteria and identify said bacteria. More specifically, the analysis unit 110 determines the value of an indicator in order to compare the value of said indicator with a determined threshold value. Depending on the result of the comparison, the analysis unit 110 determines either the presence of the bacteria or the absence of the bacteria within the Petri dish.

Figure 4:
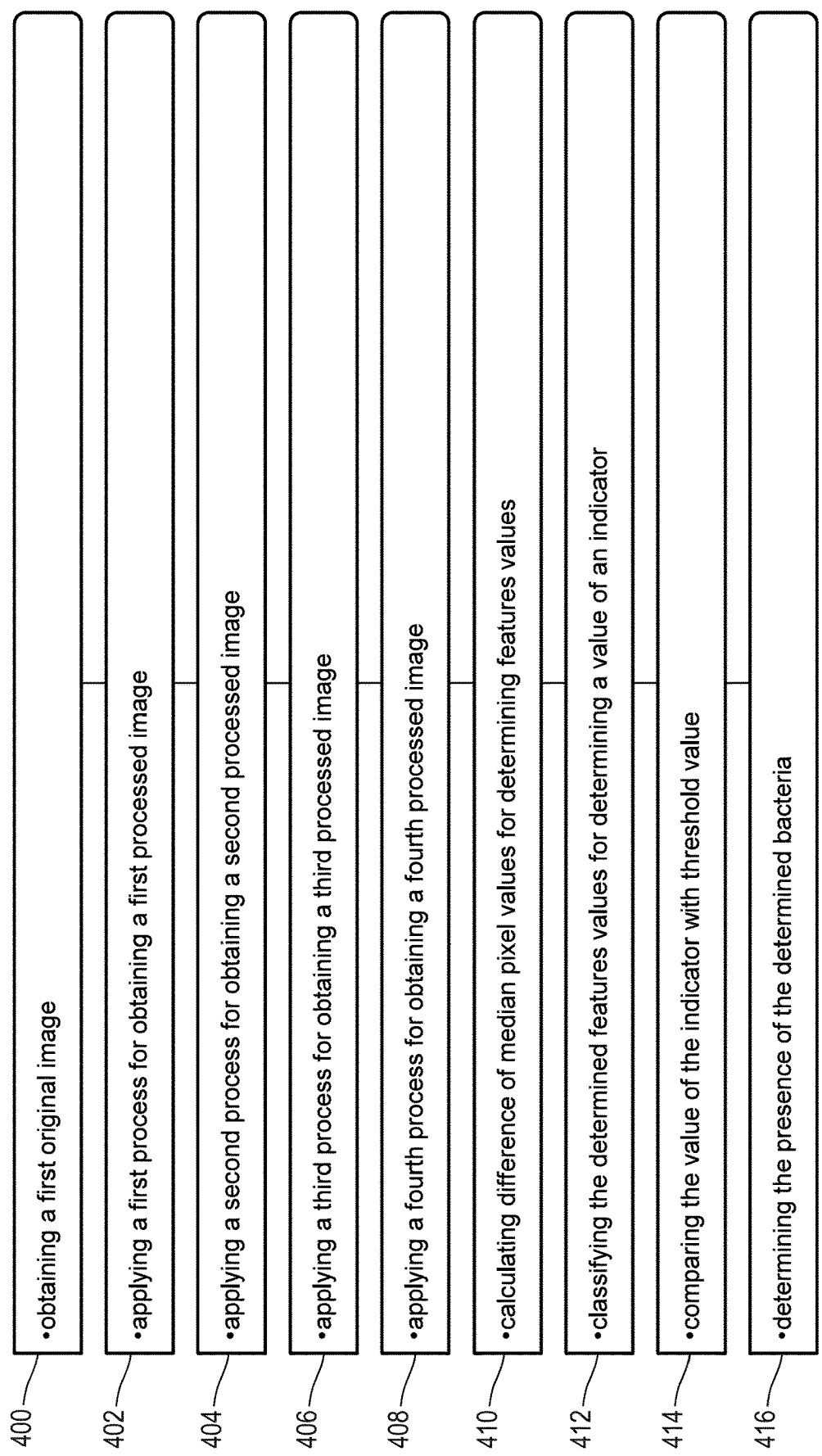
FIG. 4 shows a flowchart of the method for determining the presence of bacteria, according to an embodiment of the present invention.

According to the present invention, as shown in FIG. 4, the method comprises a step 400 for obtaining an original image of the Petri dish, with the imaging system 114, according to specific illumination conditions. Indeed, the illumination conditions may vary according to the type of bacteria to be identified. The original image may be processed to detect the edge of the Petri dish, for example.

The method then comprises a step 402 for obtaining a first processed image by applying the first process, which is a segmentation process, on the original image to obtain a first image named GrowthMask. Then, the method comprises a step 404 for obtaining a second processed image by applying the second process, which is a dilation process, on the first processed image to obtain a second image named Dilated (GrowthMask). The method comprises a further step 406 for obtaining a third processed image by applying the third process to obtain a third image named CultureMediumMask. The method also comprises a step 408 for obtaining a fourth processed image by applying the fourth process to obtain a fourth image named HaloMask. The method further comprises a step 410 for determining features values associated with the third processed image and the fourth processed image to determine the colour difference between both third and fourth processed images. The method also comprises a step 412 for determining the value of an indicator by classifying the features values. The value of the indicator is then compared to a threshold value in a step 414. The method comprises a final step 416 to determine the presence of bacteria and to identify said bacteria in the Petri dish as being the determined bacteria.

In a first embodiment of the present invention, the method relates to the determination of the presence of beta-haemolytic bacteria to identify the haemolysis phenomenon. The method of the first embodiment comprises the steps below as show in FIG. 5.

In the first embodiment, the HaloMask relates to a halo zone showing a discolouring or a faded zone around the colonies of microorganisms which is a characteristic of the haemolysis phenomenon. The discolouring zone arises from the colour of the microorganisms in the same image. The culture medium is blood agar.

In the first embodiment, the method comprises a step 500 for obtaining an initial image made of the combination of the images shown in FIGS. 7a, 7b and 7c. The initial image is obtained by using the median bottom annular view for the RGB colour channels with the imaging system 114. Indeed, the haemolysis phenomenon is less visible in images taken with this view, specifically on the green and blue colour channels. FIG. 7a shows an original image for the red colour channel. FIG. 7b shows the original image for the green colour channel and FIG. 7c shows the original image for the blue colour channel.

The method then comprises a step 502 for determining the edge of the Petri dish with a well-known edge detection method and a step for removing image noise with the well-known Gaussian filter, where $\sigma=1$ and $k=5\times5$.

The method then comprises a step 504 for separating each colour channel and a step 506 for combining the images from the green and blue colour channels with the average values of pixels for both images to provide an average image. Indeed, the removal of the image from the red colour channel avoids considering the halo zone as colonies of microorganisms.

The method further comprises a segmentation process comprising the step below. The segmentation process comprises the determination of a threshold value in step 508 according to the well-known Otsu method based on the combined image of the green colour channel image and the blue colour channel image. Indeed, the Otsu method provides a threshold value called threshold (Otsu) to compare the average value of the pixel value at a position (x, y) on determined images. More specifically, the Otsu method provides a threshold value which minimises the ratio related to the intra-class variance and the inter-class variance wherein the bright pixels values relate to the first class and the dark pixel values relate to the second class. In the present situation, the bright pixels relate to the colonies of microorganisms and the dark pixels relate to the culture medium.

The method then comprises a step 510 for segmenting the median bottom annular image by applying the following segmentation formula (1):

$$Is(x, y) = \begin{cases} 1, & \overline{I(x, y)} > \text{threshold}(Otsu) \\ 0, & \overline{I(x, y)} \leq \text{threshold}(Otsu) \end{cases} \quad (1)$$

where $\overline{I(x, y)}$ is the average value of a same pixel at a location (x,y) on a same image for the green and blue colour channels.

The application of the Otsu method provides a binary image.

The method also comprises an optional step 512 for applying a morphological operation based on a well-known closing operator on the binary image to obtain a binary image called Growth Mask as shown in FIG. 8.

The method according to the first embodiment then comprises another step 514 for obtaining a second original image shown in FIG. 6, by using the backlight view with the imaging system 114. Indeed, the haemolysis phenomenon is more visible in images taken with this view wherein the zone related to the culture medium is red, the discolouring zone is transparent with a colour being white or yellow or a composite colour made of yellow and white, and the zone related to the microorganisms is dark such as black colour.

The method comprises a step 516 for applying a well-known dilation operation on the Growth Mask, said dilation operation being based on a structuring element such as a disk shaped element. The dilation operation is operated with a well-known function such as the matlab function imdilate and with a specific dilation parameter d to obtain a corresponding dilated image of the GrowthMask called Dilated (GrowthMask).

Figure 9A:
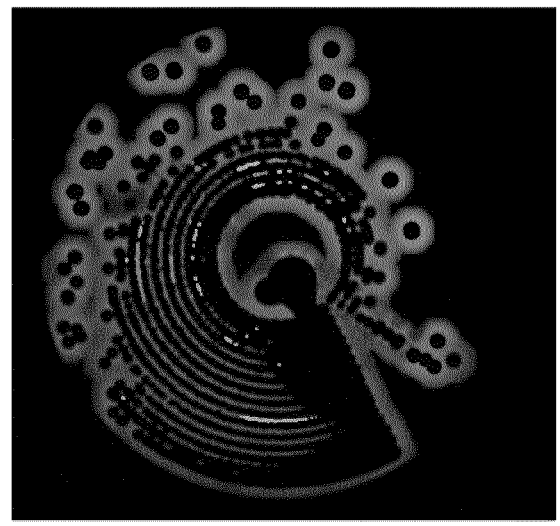
FIG. 9*a* shows an image related to the HaloMask of the original image of FIG. 6, according to an embodiment of the present invention.
Figure 9B:
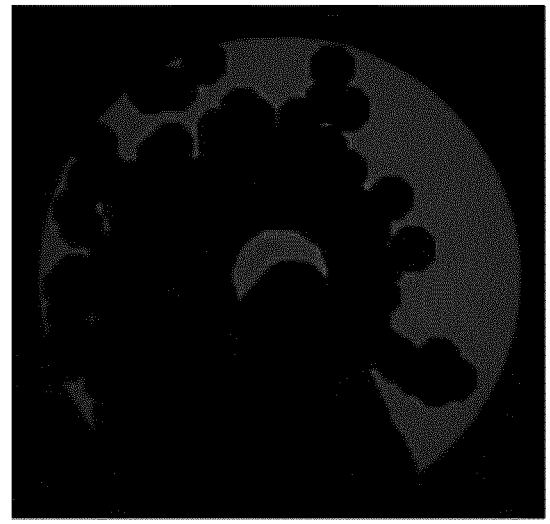
FIG. 9*b* shows a CultureMediumMask of the original image of FIG. 6 according to an embodiment of the present invention.

The HaloMask shown in FIG. 9a and the CultureMediumMask shown in FIG. 9b can be deduced from the Dilated (GrowthMask) as indicated below:

HaloMask=Dilated(GrowthMask)−GrowthMask wherein the colonies of microorganisms shown in the GrowthMask are removed from the Dilated(GrowthMask) to provide the HaloMask.

CultureMediumMask=DishMask−Dilated(Growth-Mask)

wherein the colonies of microorganisms and the halo zone related to the haemolysis phenomenon are removed from the DishMask to provide the CultureMediumMask.

The HaloMask shows the colour around the colonies of microorganisms.

The CultureMediumMask shows the original colour of the culture medium i.e. the colour which has not been impacted by the growth of microorganisms.

Figure 10A:
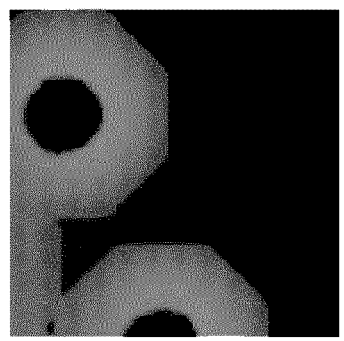
FIGS. 10*a* and 10*b* respectively show a HaloMask and a CultureMediumMask for a pixel patch of 200×200 pixels with a dilation parameter of 50 pixels, according to an embodiment of the present invention.
Figure 10B:
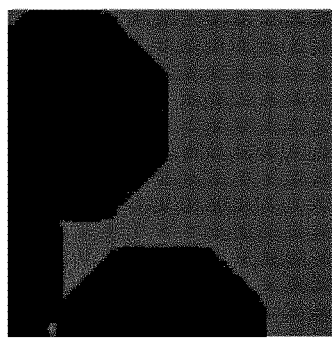

In a next step 518, the HaloMask and the CultureMediumMask are each divided into pixel patches. FIG. 10a shows a pixel patch of the HaloMask and FIG. 10b shows a pixel patch of the CultureMediumMask. In FIGS. 10a and 10b each pixel patch comprises 200×200 pixels and the size of the dilation is 50 pixels. The size of the pixel patch is adapted to detect relevant median values.

The division of the HaloMask and the CultureMediumMask is processed with an overlap rate of 50% between two adjacent pixel patches for the HaloMask and two adjacent pixel patches for the CultureMediumMask. Thus, the number of pixel patches comprising both halo pixels and culture medium pixels is optimised.

In addition, a criterion is set for pixel patches related to the HaloMask. The pixel patches wherein the halo zone comprises an area containing less than 100 pixels are not considered for the next steps of the method.

In a further step 520, the median pixel values of the HaloMask and the CultureMediumMask are computed for each pixel patch, for each channel of the RGB colour space and for greyscale representation.

The calculation of the difference of the statistical median pixel values for the HaloMask and the CultureMediumMask is processed several times based on increasing values of the dilation parameter d.

The determination of the dilation parameter d to be selected for the next steps is then processed in step 522.

The determination of the dilation parameter d is based on the following formula to determine the value of the dilation parameter d which maximises the difference value between the pixel values of the HaloMask and the pixel values of the CultureMediumMask. The dilation formula (2) below is applied for each RGB colour channel and the grayscale representation:

dilation max=argmax|Median(HaloMask*d*)−Median (CultureMediumMask*d*)| for *d*∈[10;60]  (2)

The increasing values of the dilation parameter are selected in an interval from 10 pixels to 60 pixels, with a step of 10 pixels for two consecutive values of d.

The step 522 provides a plurality of binary images called Dilated(GrowthMask) and therefore a plurality of HaloMask and CultureMediumMask.

Figure 11A:
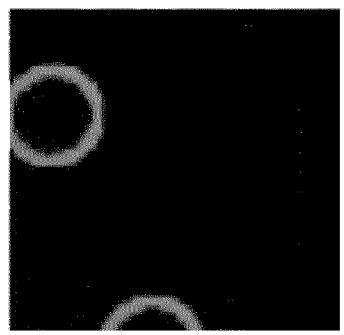
FIGS. 11*a*, 12*a* and 13*a* respectively show a pixel patch of a HaloMask with a dilation parameter of 10 pixels, 50 pixels and 60 pixels, according to an embodiment of the present invention.
Figure 12A:
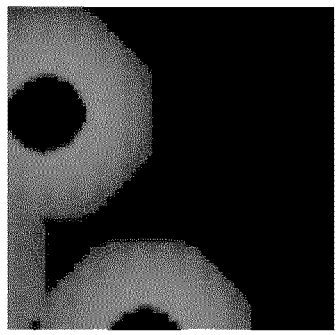
Figure 13A:
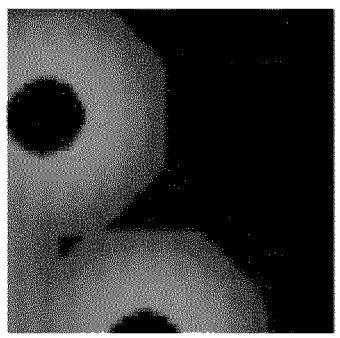

FIGS. 11a, 12a and 13a respectively show an example of a HaloMask with different values of the dilation parameter d wherein d=10 pixels in FIG. 11a, d=50 pixels in FIG. 12a and d=60 pixels in FIG. 13a.

Figure 11B:
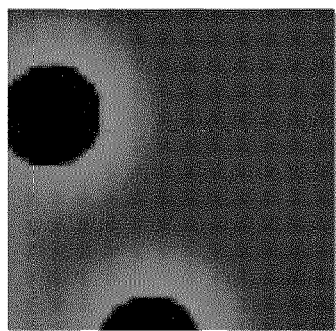
FIGS. 11*b*, 12*b* and 13*b* respectively show a pixel patch of a CultureMediumMask with a dilation parameter of 10 pixels, 50 pixels and 60 pixels, according to an embodiment of the present invention.
Figure 12B:
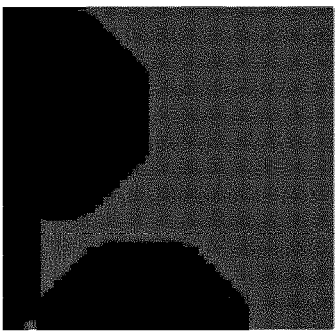
Figure 13B:
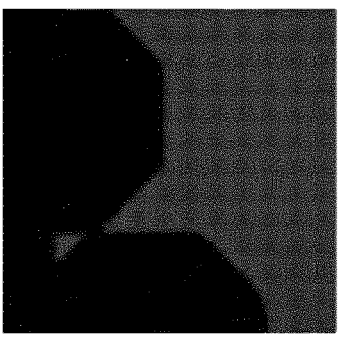

FIGS. 11b, 12b and 13b respectively show an example of a CultureMediumMask with different values of the dilation parameter d wherein d=10 pixels in FIG. 11b, d=50 pixels in FIG. 12b and d=60 pixels in FIG. 13b.

In the present situation, the determined dilation parameter is d=50 pixels.

Based on the determined dilation parameter, the difference of median pixel values for a same channel between the HaloMask and the CultureMediumMask is computed in step 524 by applying the following features formula (3) which provides four difference values between median values for the RGB colour channel and median values for the grayscale representation:

Features patch=Median(HaloMask)−Median(Culture-MediumMa  (3)

In a further step 526, the analysis unit 110 operates a step for classifying the features patch values according to a determined rule which sets a threshold value calculated with the expectation formula (4) below:

$$\text{Expectation} = \begin{cases} \text{Beta}, & \exists \text{ Features patch} > \text{threshold} \\ \text{NoBeta}, & \text{otherwise} \end{cases} \quad (4)$$

Where Features patch is the difference value of median pixel values between the HaloMask and the CultureMediumMask on blue channel.

Figure 14A:
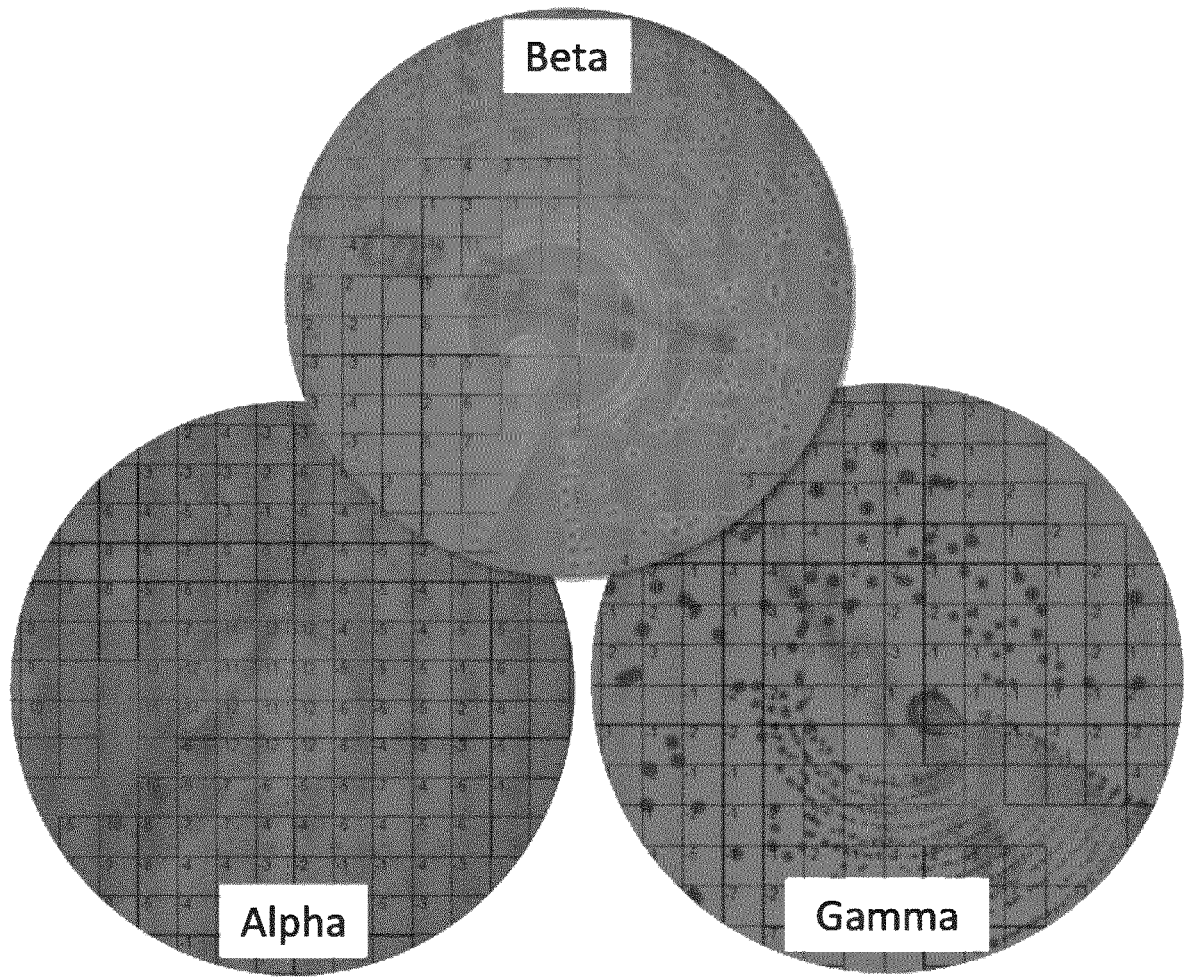
FIG. 14*a* shows a distribution of features at a patch level in a Petri dish comprising beta-haemolytic bacteria, alpha haemolytic bacteria and gamma haemolytic bacteria, according to an embodiment of the present invention.

FIG. 14a show images of a Petri dish respectively related to beta-haemolytic bacteria, alpha-haemolytic bacteria and gamma haemolytic bacteria with the representation of features values at a patch level on blue channel.

The set of values related to the Expectation formula represents the distribution of the Beta haemolysis patches and the NoBeta haemolysis patches wherein the Beta haemolysis patches comprise a halo zone representative of the haemolysis phenomenon and the NoBeta haemolysis patches do not comprise a halo zone representative of the haemolysis phenomenon.

Figure 14B:
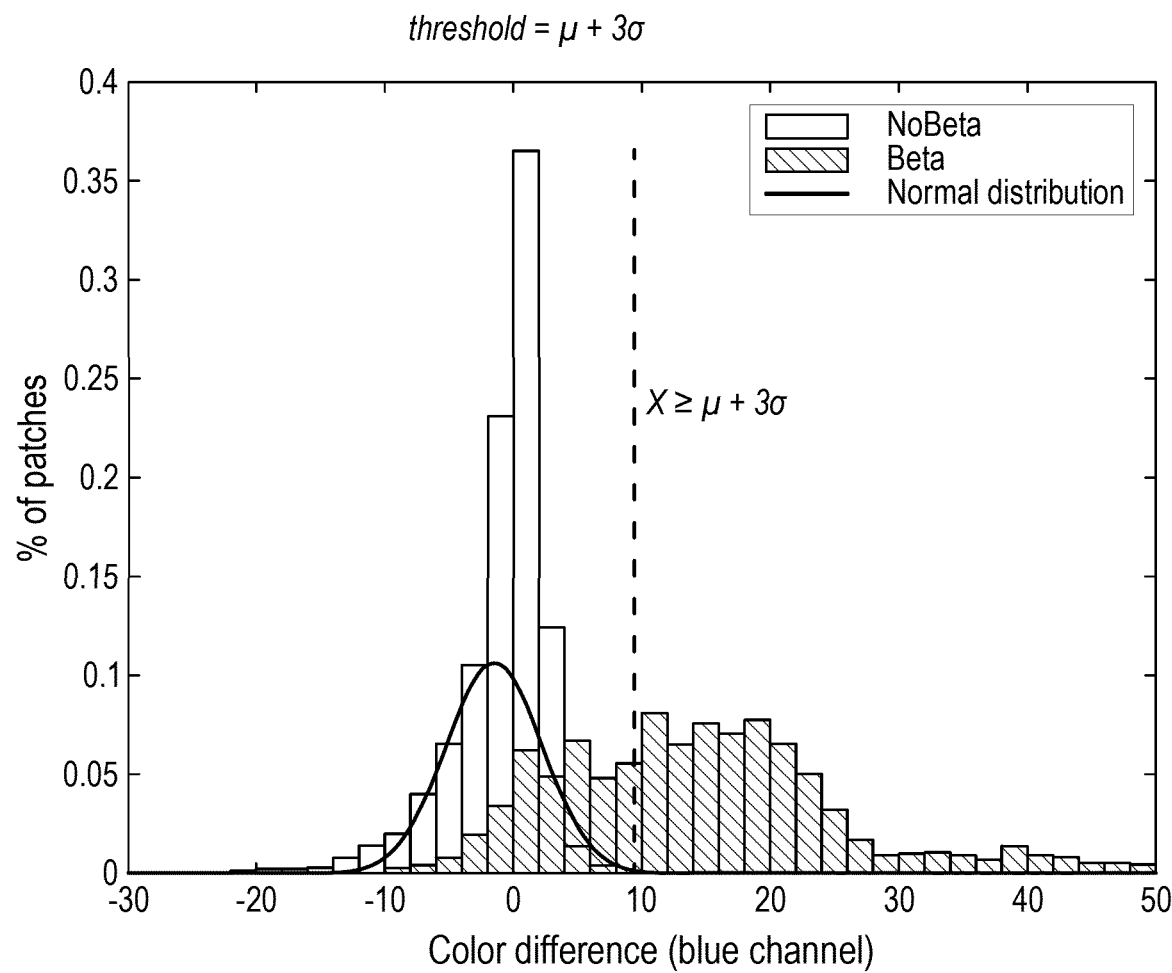
FIG. 14*b* represents a graph showing the distribution of pixel patches regarding the difference value of the colour between the HaloMask and the CultureMediumMask on the blue colour channel, according to an embodiment of the present invention.

In step 528, the distribution of NoBeta haemolysis patches is compared to a Gaussian distribution based on the mean µ and the standard deviation a as shown in FIG. 14b.

A threshold value shown in FIG. 14b and based on the 3σ rule (5) below is set to determine a normal distribution as indicated below:

$$P(\mu-3\sigma \leq x \leq \mu+3\sigma) \approx 0.9973 \quad (5)$$

This means that the threshold value is equal to µ+3σ.

In the step 530, the analysis unit 110 determine the presence or the absence of beta-haemolytic bacteria. If the Features patch values are high positive values, these values indicate the presence of beta-haemolytic bacteria.

If the Features patch values are negative or close to 0, these values indicate other phenomenon such as the presence of alpha-haemolytic or gamma-haemolytic bacteria.

In a further specific embodiment, the use of the pixel patches provides a method for determining the presence of the haemolysis phenomenon in a local manner i.e. in a specific zone of the image of the Petri dish.

Figure 15:
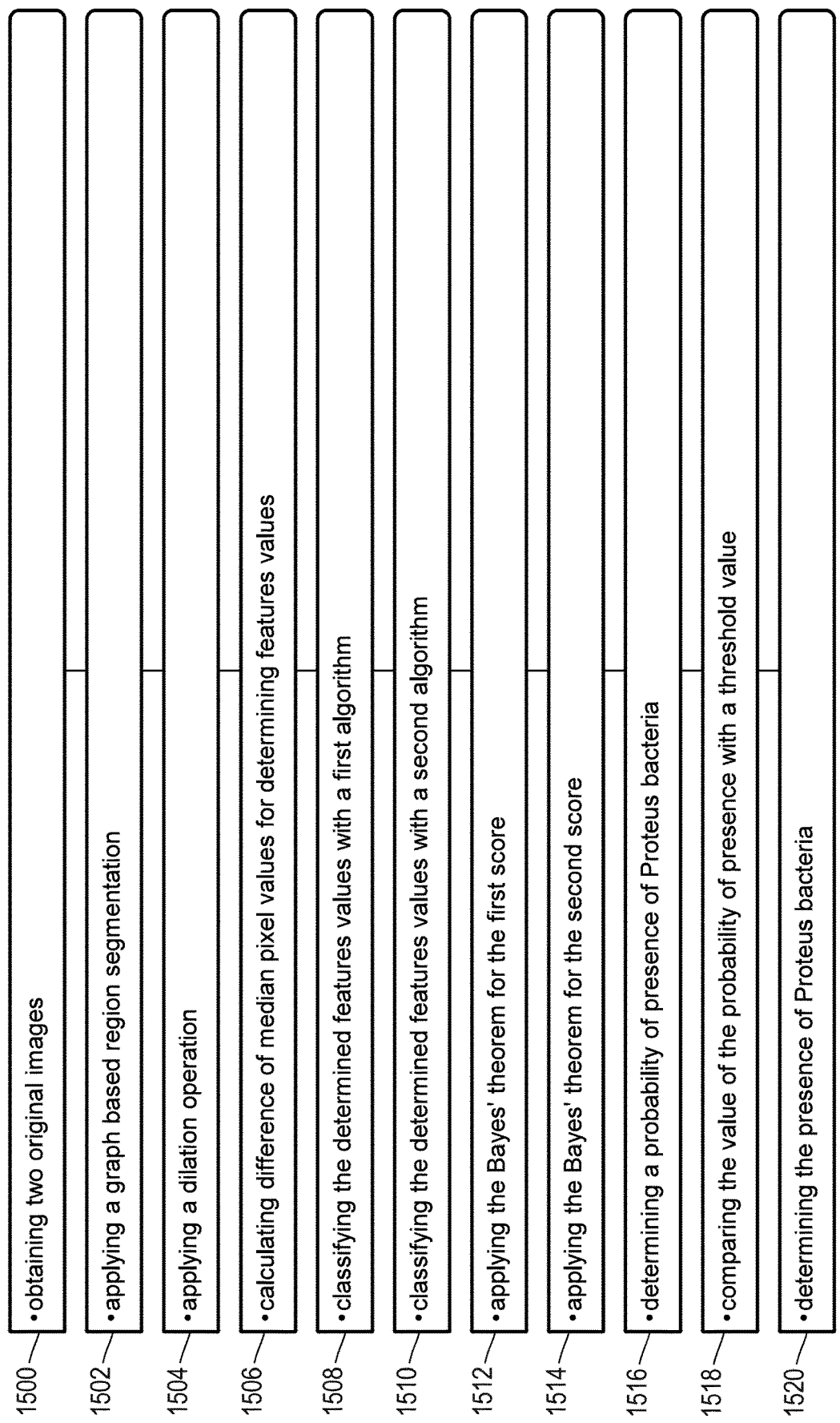
FIG. 15 shows a flowchart of the method for determining the presence of Proteus bacteria according to an embodiment of the present invention.

According to a second embodiment of the present invention related to the determination of the presence of Proteus bacteria, the method comprises the steps below as shown in FIG. 15.

In the second embodiment, the HaloMask relates to a halo zone showing a pigmentation zone around the colonies of microorganisms wherein the colour of the pigmentation zone is caused by the presence of the microorganisms in the same image. The culture medium relates to a chromogenic culture medium such as CPS.

In the second embodiment, the method comprises a step 1500 for obtaining two original views of the Petri dish by using the backlight noBackground view and the median bottom annular blackBackground view. The median bottom annular blackBackground view image is the median image of the four bottom annular side view images.

Figure 16A:
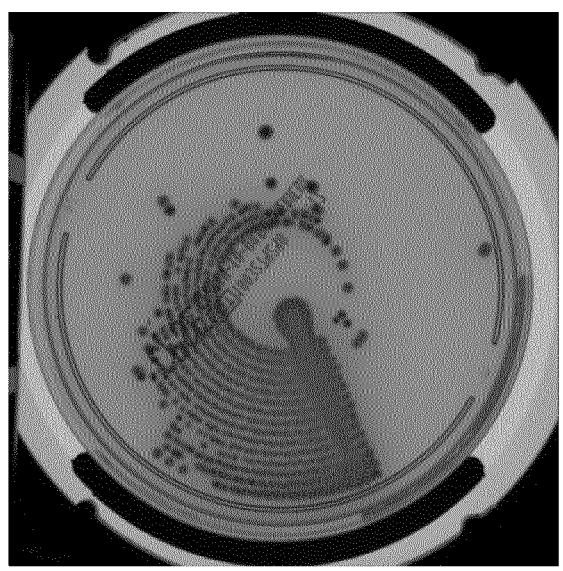
FIG. 16*a* shows an original image of a Petri dish comprising a CPS culture medium and Proteus bacteria, according to an embodiment of the present invention.

FIG. 16a shows an original image of the Petri dish by using the backlight noBackground view. In reality, FIG. 16a shows a dark zone related to the presence of colonies of microorganisms and the pigmentation zone relates to a zone having a brown colour around the dark zone.

The method then comprises a step for determining the edge of the Petri dish with a well-known edge detection method.

The method further comprises a step 1502 for applying a specific graph based region segmentation process which is disclosed in the bibliographical reference [1].

The graph based region segmentation process provides an image comprising a first region called background which relates to the culture medium zone and a second region called foreground which relates to the remainder of the Petri dish and also comprises a serigraphy zone related to the serigraphy.

Such a segmentation process segments both clusters of colonies of microorganisms colonies and isolated colonies of microorganisms within the same mask i.e. within the same foreground region. In addition, the graph based region segmentation is adapted to a slight change of colour of the culture medium zone, as in the present situation with the presence of the Proteus halo.

The segmentation process also comprises a step for detecting the serigraphy zone with a well-known detection algorithm.

Figure 16B:
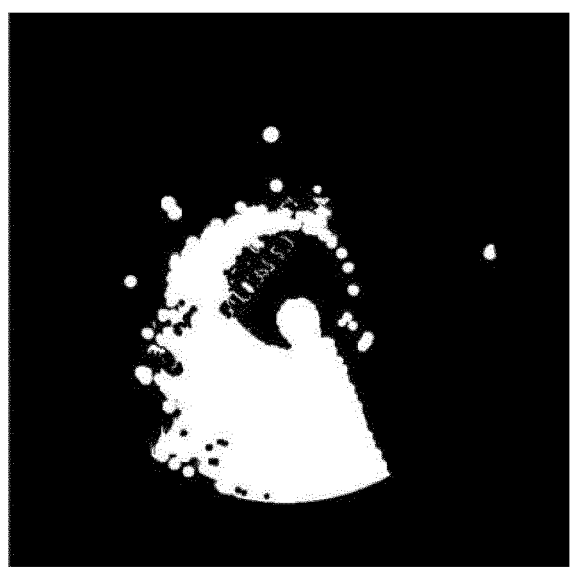
FIG. 16*b* shows a binary image called BinaryGrowth-Mask of the original image of FIG. 16*a*, according to an embodiment of the present invention.

The segmentation process then provides a binary image called GrowthMask as shown in FIG. 16b.

The method comprises a further step 1504 for applying a dilation operation to the GrowthMask, said dilation operation being based on a structuring element such as a disk shaped element. The dilation operation is operated by a well-known function such as the matlab function imdilate to produce a Dilated(GrowthMask).

The HaloMask relates to the zone which may comprise the pigmentation zone around the colonies of microorganisms, said pigmentation zone being representative of the presence of Proteus bacteria. The CultureMediumMask shows the original colour of the culture medium i.e. the colour which has not been impacted by the pigmentation zone.

Figure 17A:
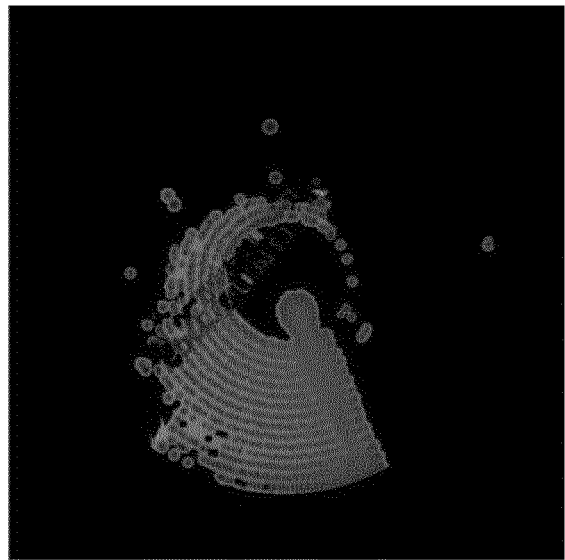
FIG. 17*a* shows a coloured GrowthMask of the original image of FIG. 16*a*, according to an embodiment of the present invention.
Figure 17B:
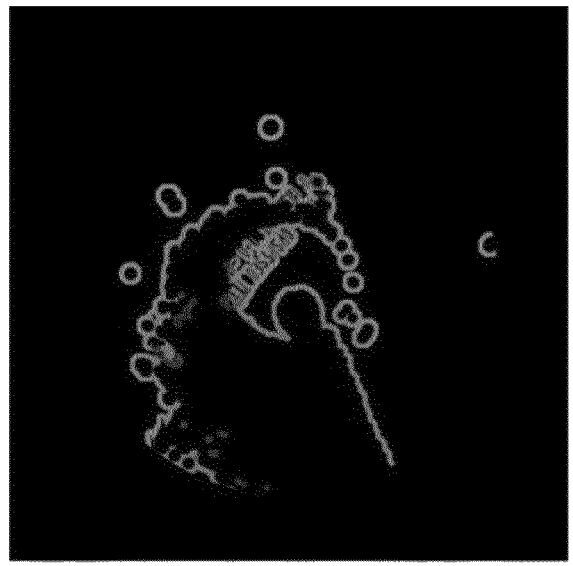
FIG. 17*b* shows a coloured HaloMask of the original image of FIG. 16*a*, according to an embodiment of the present invention.
Figure 17C:
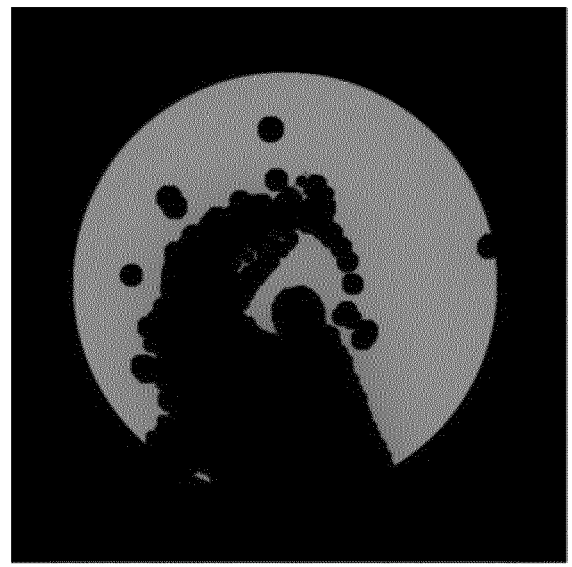
FIG. 17*c* shows a coloured CutureMediumMask of the original image of FIG. 16*a*, according to an embodiment of the present invention.

The HaloMask shown in FIG. 17b and the CultureMediumMask shown in FIG. 17c can be deduced from the Dilated(GrowthMask) and the DishMask related to the original image shown in FIG. 16a as indicated in the formulae (6) and (7) below:

$$\text{HaloMask} = \text{Dilated(GrowthMask)} - \text{GrowthMask} - \text{SerigraphyMask} \quad (6)$$

$$\text{CultureMediumMask} = \text{DishMask} - \text{Dilated(GrowthMask)} - \text{SerigraphyMask} \quad (7)$$

The dilation operation is applied several times based on increasing values of the dilation parameter d. The increasing values of the dilation parameter d are selected in an interval from 10 pixels to 70 pixels, with a step of 10 pixels for two consecutive values of d. The step 1504 provides a plurality of images called Dilated(GrowthMask).

Figure 18A:
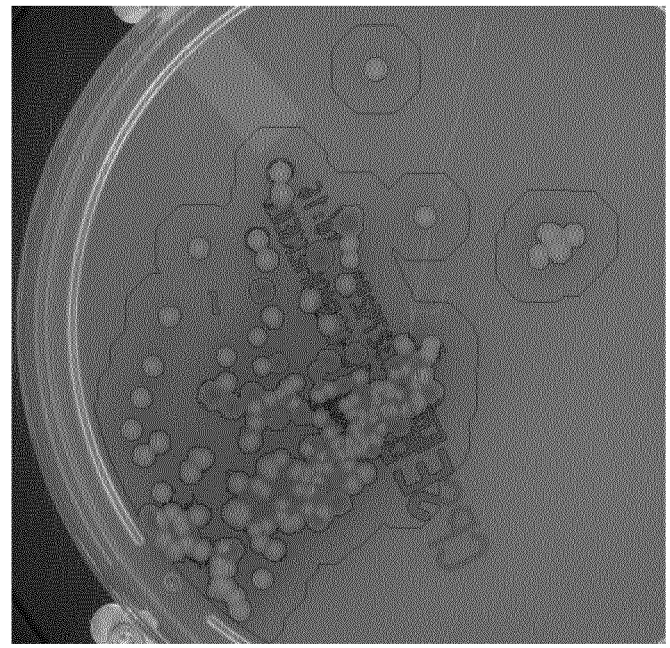
FIG. 18*a* shows the contours of HaloMask overlaid with the bottom annular view of a Petri dish comprising a CPS culture medium and bacteria of class 4 with a dilation parameter of 70 pixels, according to an embodiment of the present invention.

FIG. 18a shows an example of a HaloMask where the dilation parameter d=70 pixels.

Figure 18B:
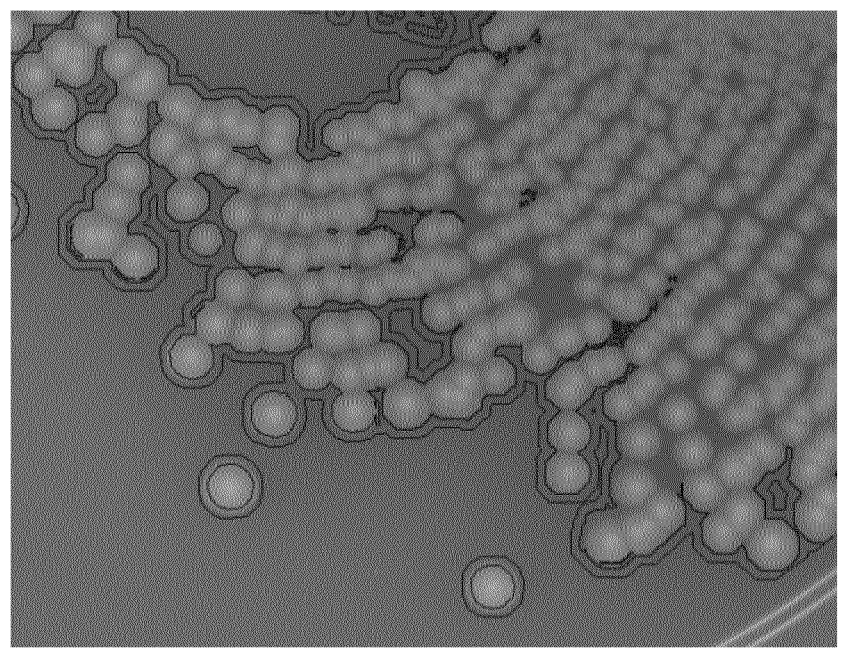
FIG. 18*b* shows the contours of HaloMask overlaid with the bottom annular view of a Petri dish comprising a CPS culture medium and bacteria of class 4 with a dilation parameter of 10 pixels, according to an embodiment of the present invention.

FIG. 18b shows an example of a HaloMask where the dilation parameter d=10 pixels.

In the following steps, the features extraction unit 120 determine the features of the HaloMask and the CultureMediumMask. Therefore, the features extraction unit 120 extracts the colour features.

The method comprises a step (not shown) for computing the statistical median value of the pixel values for the RGB colour space and the HSV (Hue, Saturation, Value) space. In the HSV space, the value H is replaced by the vector (cos H, sin H) in order to avoid the Hue scale discontinuity where 0 and 1 correspond to the same Hue value. Thus, the HSV space comprises four channels.

In order to compute the statistical median value, two different images are selected. The first image relates to the backlight noBackground view and the second image relates to the median bottom annular blackBackground view. The median bottom annular blackBackground view image is the median image of the four bottom side view images.

The method comprises a step 1506 for operating the following feature formula (8), for each RGB colour channel and each channel of the HSV space:

Feature=|Median(HaloMask)−Median(CultureMediumMask)| (8)

For the RGB colour space, there are 3 RGB colour channels where 7 dilation operations are applied on 2 different images. Thus, there are a total of 42 features being extracted when applying the above formula.

For the HSV space, there are 4 channels where 7 dilation operations are applied on 2 different images. Thus, there are a total of 56 features being extracted when applying the above formula.

Then, the global total of extracted features is 98.

Then, the analysis unit 120 operates by applying classifying steps 1508 and 1510 based on two classification algorithms used for supervised learning processes well-known in the prior art.

The first classification algorithm relates to the classification and regression tree (CART) algorithm. For example, the matlab class "ClassificationTree" is used to model CART algorithm. The application of the first algorithm provides a first score value which represents the possibility for the Petri dish to contain Proteus bacteria.

The second classification algorithm relates to the Support Vector Machine (SVM) algorithm and is generated by using the library "libSVM". The application of the second algorithm provides a second score value which represents the possibility for the Petri dish to contain Proteus bacteria.

As the first score and the second score are provided by two different classification algorithms, the first and second score are not comparable values, and cannot be combined within a same calculation to determine a final score.

The classification unit 120 operates by applying the Bayes' theorem to obtain values of a posteriori probabilities i.e. p(Halo;X) where halo is the event representing the halo.

In the first classification algorithm, X represents the value of the feature selected by the CART algorithm. The selected feature relates to a feature being the most discriminating feature to determine the presence of Proteus bacteria among the 98 existing features.

In the second classification algorithm, X represents the distance of closest example from the decision line. The highest distance X represents a reliable result for the determination of the possibility for the Petri dish to contain Proteus bacteria.

The probability of presence of the halo may be calculated with the formula (9) below:

$$p(Halo; X) = \frac{p(X; Halo) * p(Halo)}{p(X)} \quad (9)$$

where p(X;Halo) is the probability of observing X assuming the Petri dish contains a Halo;
p(Halo) is the prior probability of the presence of a halo;
and p(Halo;X) is the probability of halo presence given the value X.

If the Petri dish does not contain Proteus bacteria, the probability of having a halo is expected to be 0.

However, there may be some situations where the Petri dish contains Proteus bacteria which have no visual halo and the probability of having a halo is also equal to 0. Thus, in order to facilitate the detection of Proteus bacteria, the above formula (9) is amended to avoid considering such situations. The formula (10) below takes into account the hypothesis related to the presence of a visible halo for all Proteus bacteria.

The classification unit 120 then operates the formula (10) below:

$$p(Halo; X) = \frac{p(X; Proteus) * p(Proteus)}{p(X)} \quad (10)$$

where p(X;Proteus) is the probability of having X assuming the Petri dish contains Proteus bacteria;
and p(Proteus) is the a priori probability of the presence of Proteus bacteria.

Figure 19:
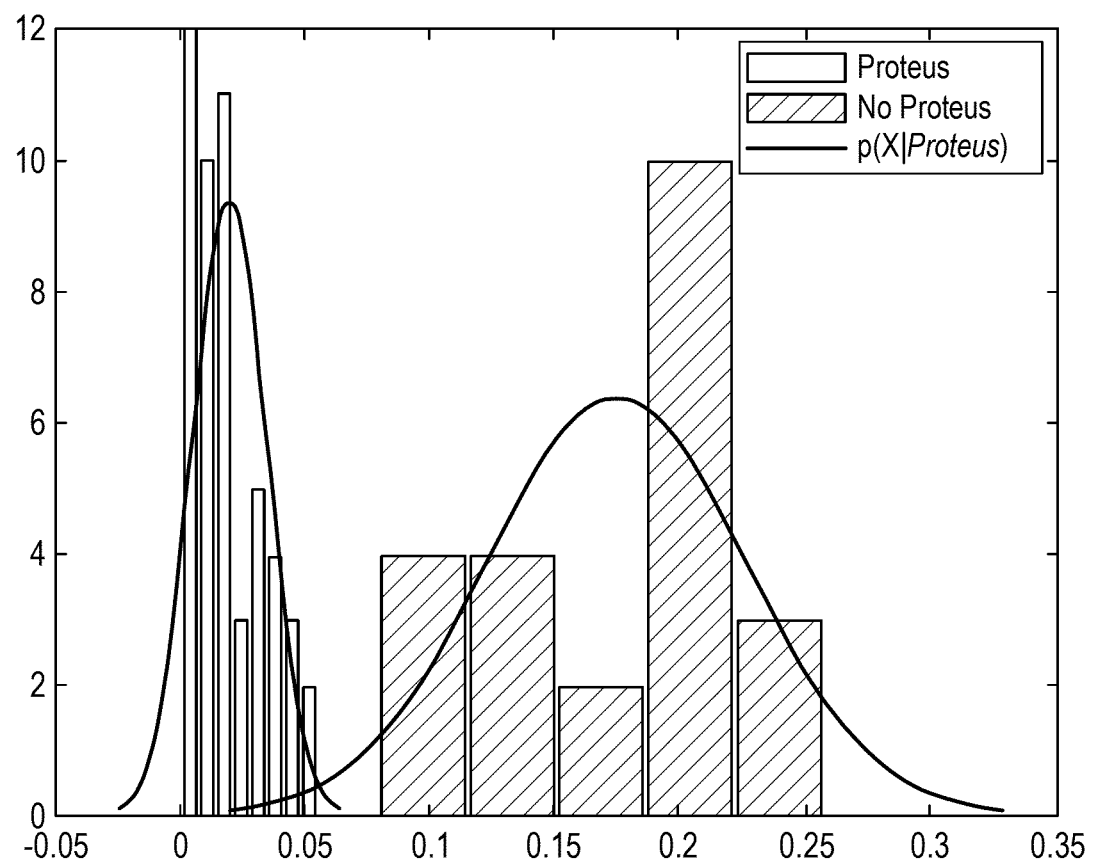
FIG. 19 shows a graph representing the distribution of the probability of presence of Proteus bacteria, according to an embodiment of the present invention.

The set of values related to the probability p(X;Proteus) is represented in FIG. 19 as a distribution of values based on a Gaussian distribution with the mean p and the standard deviation σ.

p(Proteus) is the prior probability and is an adjustable parameter set to ⅙ by default. Indeed, a CPS culture medium may contain up to six classes of bacteria.

p(X) is an estimated value of a normalising factor calculated with the formula (11) below where:
p(Proteus), p(X;Proteus), p(NoProteus) and P(X;NoProteus) are known from the set of data used for the supervised learning process.

$$p(X)=p(Proteus)*p(X;Proteus)+p(Proteus)*p(X;Proteus) \quad (11)$$

Thus, in a further step 1512, a first value of p(Halo;X) is calculated with the first score related to the first classification algorithm, i.e. the CART algorithm.

In a further step 1514, a second value of p(Halo;X) is calculated with the second score related to the second classification algorithm, i.e. the SVM algorithm.

Thus, the first and the second values of p(Halo;X) relate to first and a second probabilities which are now same type of values i.e. comparable values.

The minimum values of the first and the second values of p(Halo;X) are obtained and the lowest minimum values between the first and second values of p(Halo;X) is selected in a further step 1516.

Then a final probability of presence of Proteus bacteria between 0% and 100% is obtained in step 1516.

The user can decide to use threshold value such as 50% to determine the probability of presence of Proteus bacteria in the Petri dish in step 1520 by comparing the value of the probability of presence of Proteus bacteria in step 1518.

The use of the two probabilities respectively based on the first classification algorithm and on the second classification algorithm provides a correction of the errors independently produced by each classification algorithm.

In another embodiment related to the determination of the presence of Proteus bacteria, the culture medium may be an opaque culture medium such as an opaque CPS.

FIG. 20 shows an original image of a Petri dish containing an opaque culture medium such as an opaque CPS with Proteus bacteria and related to a backlight view.

FIGS. 21 and 22 show an image of the Petri dish of FIG. 20 respectively related to left bottom annular view and top annular view.

A further embodiment of the present invention relates to the above described method related to the detection of Proteus bacteria wherein the culture medium is an opaque culture medium.

The steps 1500 and the steps 1504 to 1520 related to the above method remain the same. The step 1502 step related to the application of a segmentation process has to be adapted to take into account the presence of the opaque culture medium.

Indeed, in the presence of an opaque culture medium, the segmentation process includes the application of an adapted graph based region segmentation algorithm and the steps related to the detection and the removal of the serigraphy zone are removed.

In this embodiment, the images used as original images are based on backlight view and top annular view. Other parameters such as the way to combine said original images and the threshold values related to the foreground extraction process are adapted to allow the method related to the detection of Proteus bacteria with an opaque culture medium to operate in an efficient manner.

The description below relates to the application of the method of the present invention regarding the detection of beta-haemolytic bacteria and the detection of Proteus bacteria.

The method related to the detection of beta-haemolytic bacteria has been applied on a first dataset comprising Petri dishes containing mono-bacterial colonies and blood agar culture media such as COS and CAN culture media, said Petri dishes having been incubated for 24 hours.

The first dataset comprises a total number of 104 Petri dishes wherein, according to the ground truth reference, 21 Petri dishes contain beta-haemolytic bacteria and 83 Petri dishes contain no beta-haemolytic bacteria, i.e. bacteria other than beta-haemolytic bacteria.

Table 1 below shows the results of the application of the method on said first dataset, wherein 14 Petri dishes among a total number of 21 Petri dishes have been identified as containing beta-haemolytic and 83 Petri dishes among a total number of 83 Petri dishes have been identified as not containing beta-haemolytic bacteria:

TABLE 1

| Results by Petri dishes in numbers for the first dataset | | Automated recognition | |
|---|---|---|---|
| | | Beta | NoBeta |
| Ground truth | Beta | 14 | 7 |
| | NoBeta | 0 | 83 |

From Table 1, it appears that 7 Petri dishes that contain beta-haemolytic bacteria have not been detected and identified when applying the method according to the invention. Indeed, the halo zone within the corresponding Petri dishes is not clearly visible and therefore the difference of colour between the halo zone and the culture medium zone for said Petri dishes does not provide a sufficient contrast level to determine the presence of haemolytic bacteria.

Table 2 below shows the same results as the one shown in Table 1 by using a percentage as an indicator and a confidence interval of 95%:

TABLE 2

| Results by Petri dishes in % for the first dataset | | Automated recognition | |
|---|---|---|---|
| | | Beta | NoBeta |
| Ground truth | Beta | 66.7% [45.4%-82.8%] | 33.3% |
| | NoBeta | 0% | 100% [95.6%-100%] |

According to the above Table 2, the global accuracy percentage is higher than 93%.

The method related to the detection of beta-haemolytic bacteria has also been applied on a second dataset comprising Petri dishes containing mono-bacterial colonies and blood agar culture media such as COS and CAN culture media, said Petri dishes having been incubated for 24 hours.

The second dataset comprises a total number of 70 Petri dishes wherein, according to the ground truth reference, 24 Petri dishes contain beta-haemolytic bacteria and 46 Petri dishes contain no beta-haemolytic bacteria, i.e. bacteria other than beta-haemolytic bacteria.

Table 3 below shows the results of the application of the method on said second dataset, wherein 23 Petri dishes among a total number of 241 Petri dishes have been identified as containing beta-haemolytic and 43 Petri dishes among a total number of 46 Petri dishes have been identified as not containing beta-haemolytic bacteria:

TABLE 3

| Results by Petri dishes in numbers for the second dataset | | Automated recognition | |
|---|---|---|---|
| | | Beta | NoBeta |
| Ground truth | Beta | 23 | 1 |
| | NoBeta | 3 | 43 |

From Table 3, it appears that 1 Petri dish that contains beta-haemolytic bacteria has not been detected and identified when applying the method according to the invention. Indeed, the Petri dish only contains one colony of microorganisms and the segmentation process has not provided a correct CultureMediumMask and a correct HaloMask.

From Table 3, it also appears that 3 false detections of beta-haemolytic bacteria have occurred. These false detections may be generated by the presence of a halo zone around colonies of gamma haemolytic bacteria or by the presence of the serigraphy zone or by the presence of the edge of the Petri dish. However, such false detections may be retrieved in the step of the method related to the determination of the threshold value according to the Otsu's method.

Table 4 below shows the same results as the one shown in table 1 by using a percentage as an indicator and with a confidence interval of 95%:

TABLE 4

| Results by Petri dishes in % for the second dataset | | Automated recognition | |
|---|---|---|---|
| | | Beta | NoBeta |
| Ground truth | Beta | 95.8% [79.7%-99.3%] | 4.2% |
| | NoBeta | 6.5% | 93.5% [82.5%-97.7%] |

According to the above Table 4, the global accuracy percentage is higher than 94%.

The results shown in Tables 1, 2, 3 and 4 indicate a high level of 95% of accuracy for the method of the present invention for the detection of beta-haemolytic bacteria.

The method related to the detection of Proteus bacteria has been applied on a first data set related to Petri dishes which contain mono-bacterial colonies and mixtures of bacteria from two different classes of bacteria and a translucent chromogenic culture medium, said Petri dishes having been incubated for 24 hours.

The first dataset comprises Proteus bacteria having a halo zone and Proteus bacteria that do not have a halo zone.

As described above, the method according the present invention for the detection of Proteus bacteria comprises a step for classifying the features by using two supervised model algorithms to separate the features data into two different classes which are the presence of the halo zone or the absence of the halo zone. The same data set is used for each supervised model algorithm.

The analysis of the results is based on the Table 5 below which is a confusion matrix to determine the confusing level of the used supervised model:

TABLE 5

|  |  | Results | |
|---|---|---|---|
|  |  | Halo | No Halo |
| Ground Truth | Proteus | True positive | False negative |
|  | No Proteus | False positive | True negative |

In the present situation, the available ground truth is the presence of Proteus bacteria or the absence of Proteus bacteria whereas the method provides a prediction related to the presence or the absence of a halo zone.

When considering the learning model related to the classification and regression tree, the results shown in Table 6 below are obtained:

TABLE 6

| First dataset and translucent | | Results | |
|---|---|---|---|
| culture medium | | Halo | No Halo |
| Ground truth | Proteus | 78% | 22% |
|  | No Proteus | 1% | 99% |

Table 6 indicates that the level of accuracy is 99% which is a very good level. The level of sensitivity is 78/% which is also a good level. As mentioned above, the dataset comprises Petri dishes containing Proteus bacteria that do not have a halo zone. A visual check of the 22% of Petri dishes mentioned in Table 6 indicates that a majority of said Petri dishes contains Proteus bacteria that do not have a halo zone. It also appears that boundaries of colonies are incorrectly detected as being a halo zone by the supervised model algorithm. However, the use of the statistical median pixel value overcomes this issue.

When considering the learning model related to the SVM, the results shown in Table 7 below are obtained:

TABLE 7

| First dataset and translucent | | Results | |
|---|---|---|---|
| culture medium | | Halo | No Halo |
| Ground truth | Proteus | 74% | 26% |
|  | No Proteus | 1% | 99% |

The percentage of Petri dishes which have a halo zone and do not contain Proteus bacteria differs from the corresponding percentage retrieved in Table 6 for the classification and regression tree.

When considering an opaque culture medium, the results related to the detection of Proteus bacteria are quite similar to those retrieved with a translucent culture medium. In addition, as the halo zone is more visible in Petri dishes comprising an opaque culture medium, the method provides less false negative detection i.e. Proteus bacteria classified as No Halo.

From the disclosure: CART keeps its unique node, with the same feature chosen, with a unique size of dilatation equal to 10 pixels.

Table 8 below shows an example of a confusion matrix for the application of the SVM algorithm:

TABLE 8

| First dataset and opaque | | Results | |
|---|---|---|---|
| culture medium | | Halo | No Halo |
| Ground truth | Proteus | 90% | 10% |
|  | No Proteus | 1% | 99% |

As explained above in reference to the embodiment of the detection of Proteus bacteria, the confidence indicator is a percentage which is calculated with the Bayes' theorem by using the a posteriori probability as provided by the two supervised model algorithms, CART and SVM. The values of the confidence indicators belong to an interval [0; 100] wherein 0% means that there is no halo zone and 100% means that there is a halo zone in the Petri dish.

As mentioned above, $$p(Halo; X) = \frac{p(X; Proteus) * p(Proteus)}{p(X)}$$

where p(X;Proteus) is the probability of having X assuming the Petri dish contains Proteus bacteria with X being the distance to the margin;
and p(Proteus) is the a priori probability of the presence of Proteus bacteria.

Figure 23:
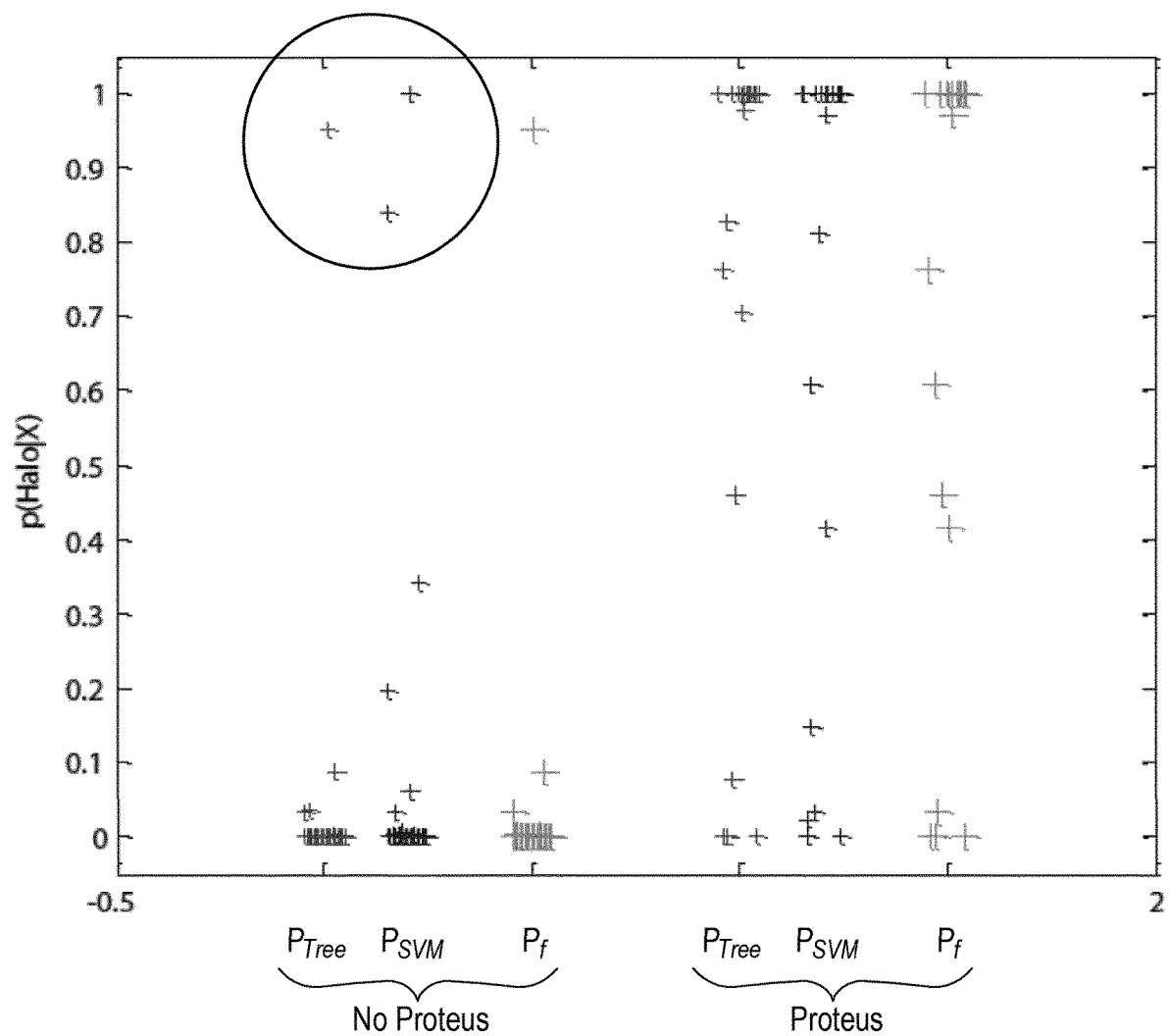
FIG. 23 represents a graph showing the distribution of the probabilities p(Halo/X) of the presence of Proteus bacteria with the CART algorithm and the SVM algorithm and the distribution of the final probabilities of the presence of Proteus bacteria for Petri dishes containing a translucent culture medium, according to an embodiment of the present invention.

FIG. 23 shows the distribution of the resulting probabilities for both supervised model algorithms, CART and SVM, showing the probabilities for Petri dishes that contain Proteus bacteria and for Petri dishes that do not contain Proteus bacteria with a translucent culture medium in both situations.

The circle indicates the detection of false positive results shown in Tables 6 and 7.

FIG. 23 also shows the distribution of the final probabilities which represent the merged values Pf of the lowest probabilities Ptree and Psvm for both supervised model algorithms, CART and SVM.

A threshold value of 50% is selected such as:

$$\begin{cases} \text{if } p(\text{Halo}; X) \geq 50\% \to \text{Halo} \\ \text{if } p(\text{Halo}; X) < 50\% \to \text{No Halo} \end{cases}$$

Table 9 below evaluates the results of the confidence indicators:

TABLE 9

| Translucent culture medium | | Results (% and corresponding number of Petri dishes) | |
|---|---|---|---|
| | | Halo | No Halo |
| Ground truth | Proteus | 71% 17/24 | 29% 7/24 |
| | No Proteus | <1% 1/151 | >99% 150/151 |

The above Table 9 shows that the level of accuracy is higher than 99% which is a very good level. Indeed, the merge of the results provided by the two supervised model algorithms avoids the detection of false positive.

In addition, the level of sensitivity is 71% which is also a good level as some Petri dishes contain Proteus bacteria that do not have a halo zone.

Figure 24:
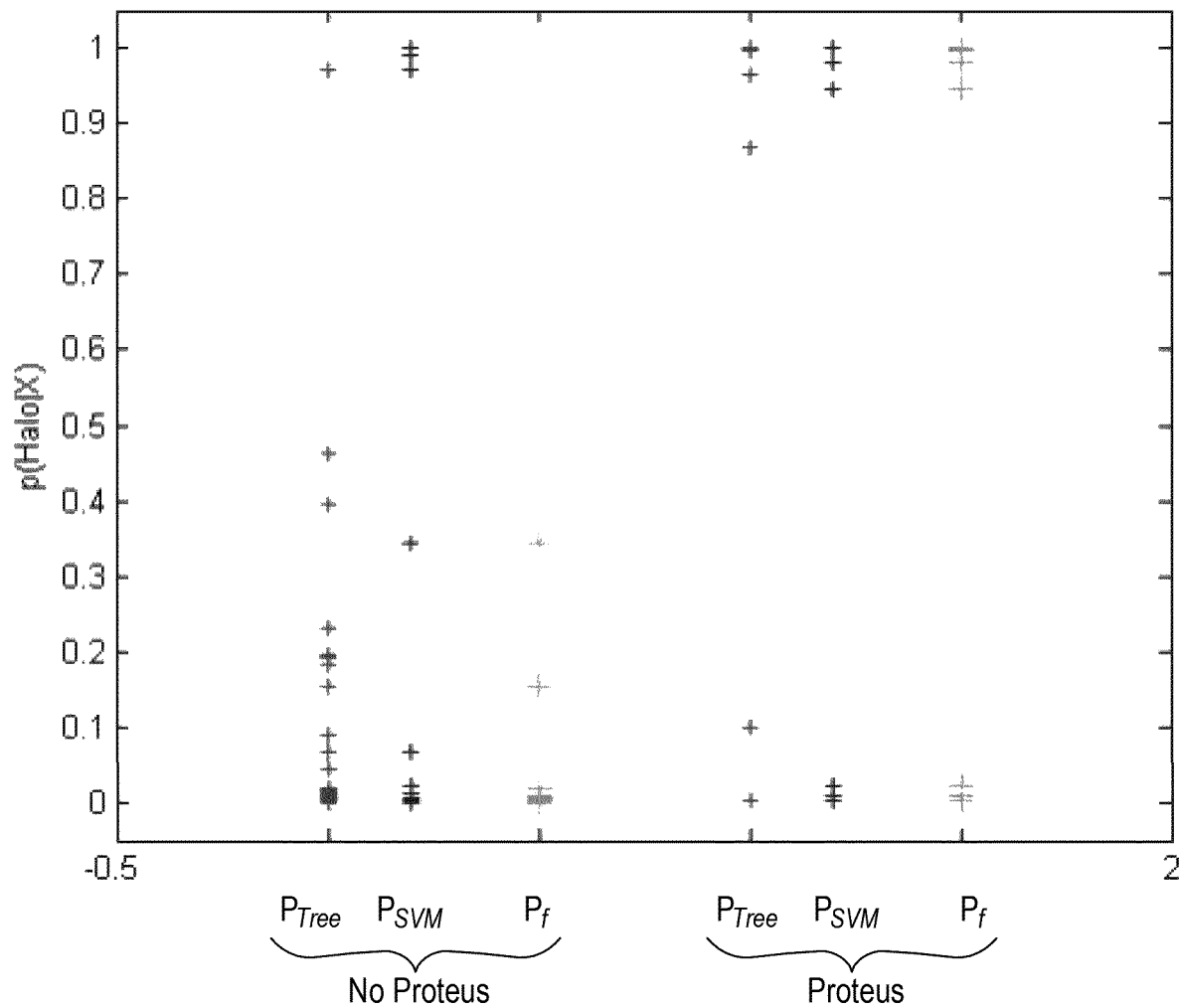
FIG. 24 represents a graph showing the distribution of the probabilities p(Halo/X) of the presence of Proteus bacteria with the CART algorithm and the SVM algorithm and the distribution of the final probabilities of the presence of Proteus bacteria for Petri dishes containing an opaque culture medium, according to an embodiment of the present invention.

FIG. 24 shows the distribution of the resulting probabilities for both supervised model algorithms, CART and SVM, showing the probabilities for Petri dishes that contain Proteus bacteria and an opaque culture medium, and for Petri dishes that do not contain Proteus bacteria with an opaque culture medium for both situations.

FIG. 24 also shows the distribution of the final probabilities which represent the merged values Pf of the lowest probabilities Ptree and Psvm for both supervised model algorithms, CART and SVM.

TABLE 10

| First dataset and opaque culture medium | | Results | |
|---|---|---|---|
| | | Halo | No Halo |
| Ground truth | Proteus | 89% 25/28 | 11% 3/28 |
| | No Proteus | 0% 0/126 | 100% 126/126 |

In another situation where the Petri dishes have been incubated for 18 hours, the results shown in Table 11 below are obtained for a translucent culture medium:

TABLE 11

| Translucent culture medium | | Results (% and corresponding number of Petri dishes) | |
|---|---|---|---|
| | | Halo | No Halo |
| Ground truth | Proteus | 74% 17/23 | 29% 6/23 |
| | No Proteus | <1% 1/141 | >99% 140/141 |

The corresponding results for an opaque culture medium are shown in Table 12 below:

TABLE 12

| Opaque culture medium | | Results (% and corresponding number of Petri dishes) | |
|---|---|---|---|
| | | Halo | No Halo |
| Ground truth | Proteus | 92% 24/26 | 8% 2/26 |
| | No Proteus | 0% 0/139 | 100% 139/139 |

As shown in the above Tables 11 and 12, the results acquired for 18 hour and 24 hour durations are stable for Petri dishes containing translucent or opaque culture medium.

BIBLIOGRAPHICAL REFERENCES

[1] Pedro F. Felzenszwalb, Daniel P. Huttenlocher, "Efficient Graph-Based Image Segmentation"; International Journal of Computer Vision, September 2004, Volume 59, Issue 2, pages 167-181

The invention claimed is:

1. A method for determining the presence of at least one determined microorganism in a Petri dish comprising one or more colonies of microorganisms and a culture medium, said culture medium being adapted to allow the one or more colonies of microorganisms and said at least one determined microorganism, if present, to grow under suitable growth conditions, the method comprising:
    obtaining at least an initial image of the Petri dish, wherein the first initial image comprises one or more visible pixels, each pixel being associated with a pixel value;
    obtaining a first processed image of the Petri dish by applying a first process to the at least one initial image, wherein visible pixels of the first processed image only relate to the pixels associated with the one or more colonies of microorganisms;
    obtaining a plurality of second processed images of the Petri dish by applying a second process to the first processed image, wherein visible pixels of the second processed image only relate to the pixels associated with the one or more colonies of microorganisms and a surrounding zone around said one or more colonies of microorganisms;
    obtaining a plurality of third processed images of the Petri dish by calculating the difference between the at least one initial image and the plurality of second processed images, wherein the plurality of third processed images comprises visible pixels which only relates to pixels associated with the culture medium;
    obtaining a plurality of fourth processed images of the Petri dish by calculating the difference between the plurality of second processed images and the first processed image, wherein visible pixels of the plurality of fourth processed images only relate to pixels associated with the surrounding zone;
    determining features values associated with the plurality of the third and the fourth processed images by calculating the difference values between the average pixel values of the plurality of the third processed image and the average pixel values of the plurality of the fourth processed image for at least each colour channel of the Red Green Blue (RGB) colour channels;

determining a value of an indicator of the presence of the at least one determined microorganism within the surrounding zone in the Petri dish by classifying the determined features values;

comparing the value of the indicator with a threshold value;

depending on the result of the comparison, determining the presence of the at least one determined microorganism within the surrounding zone in the Petri dish.

2. The method as claimed in claim 1, wherein the first process is a segmentation process.

3. The method as claimed in claim 2, wherein the segmentation process comprises the determination of a threshold value and a comparison of pixel values with said threshold value.

4. The method as claimed in claim 2, wherein the segmentation process is a graph based region segmentation process.

5. The method as claimed in claim 1, wherein the second process is a dilation process associated with a dilation criterion having a plurality of defined values.

6. The method as claimed in claim 1, wherein the step of determining features values comprises dividing the plurality of the third and fourth processed images into pixel patches.

7. The method as claimed in claim 6, further comprising calculating the maximal difference of pixel values between pixel values of the third and fourth processed images, for each pixel patch.

8. The method as claimed in claim 7, wherein the step of determining features values comprises calculating the maximal difference of pixel values for the greyscale image.

9. The method as claimed in claim 1, wherein the step of determining features values comprises calculating the median pixel values of the plurality of the first processed images and the median pixel values of the plurality of the first processed image for the HSV space.

10. The method as claimed in claim 1, wherein the step of classifying the features values comprises comparing the distribution of features values with a Gaussian distribution.

11. The method as claimed in claim 1, wherein the step of classifying the features values comprises applying a classification and regression tree algorithm and a support vector algorithm to provide a corresponding first and second score.

12. The method as claimed in claim 11, wherein the step of classifying the features values further comprises applying the Bayes theorem to the first and second score.

13. The method as claimed in claim 12, wherein the step of classifying the features values further comprises obtaining a combined possibility of presence of the surrounding zone.

14. The method as claimed in claim 1, wherein the step of comparing the value of the indicator with a threshold comprises determining a threshold value based on the mean and the standard deviation σ of the Gaussian distribution.

15. The method as claimed in claim 1 wherein the step of determining the presence of the at least determined microorganism comprises determining the presence of a bacteria being a beta-haemolytic bacteria.

16. The method as claimed in claim 1 wherein the step of determining the presence of the at least determined microorganism comprises determining the presence of a bacteria being a Proteus bacteria.

17. A system (100) for determining the presence of at least one determined microorganism in a Petri dish comprising one or more colonies of microorganisms and a culture medium, said culture medium being adapted to allow the one or more colonies of microorganisms and said at least one determined microorganism, if present, to grow under suitable growth conditions, wherein the system comprises an imaging system for obtaining at least one initial image of the Petri dish, and a processing system (108), said processing system (108) comprising:

a first processing unit (116) for obtaining a first processed image of the at least one initial image of the Petri dish, wherein visible pixels of the first processed image only relate to the pixels associated with the one or more colonies of microorganisms;

a second processing unit (118) for obtaining a plurality of second processed images of the first processed image of the Petri dish, wherein visible pixels of the second processed images only relate to the pixels associated with the one or more colonies of microorganisms and a surrounding zone around said one or more colonies of microorganisms;

a calculation unit (120) for obtaining a plurality of third processed images of the Petri dish by calculating the difference between a second initial image and the second processed images, wherein visible pixels of the third processed images only relates to pixels associated with the culture medium, and for obtaining a plurality of fourth processed images of the Petri dish by calculating the difference between the second processed images and the first processed image, wherein visible pixels of the fourth processed images only relate to pixels associated with the surrounding zone;

a features extraction unit (122) for determining features values associated with the plurality of the third and the fourth processed images by calculating the difference values between the average pixel values of the third processed images and the average pixel values of the fourth processed images for at least each colour channel of RGB colour channels;

and an analysis unit (110) for determining a value of an indicator of the presence of the at least one determined microorganism within the surrounding zone in the Petri dish, comparing the value of the indicator with a threshold value; and determining the presence of the at least one determined microorganisms within the surrounding zone in the Petri dish, depending on the result of the comparison.

18. A non-transitory computer readable medium comprising instructions which, when executed, cause a programmable data processing apparatus to perform steps of the method according to claim 1.

* * * * *